United States Patent [19]
Konrad

[11] Patent Number: 5,789,167
[45] Date of Patent: Aug. 4, 1998

[54] OPTICAL DETECTION OF POSITION OF OLIGONUCLEOTIDES ON LARGE DNA MOLECULES

[75] Inventor: Michael W. Konrad, Lafayette, Calif.

[73] Assignee: GeneVue, Inc., Lafayette, Calif.

[21] Appl. No.: 596,159

[22] PCT Filed: Sep. 8, 1994

[86] PCT No.: PCT/US94/09764

§ 371 Date: Feb. 14, 1996

§ 102(e) Date: Feb. 14, 1996

[87] PCT Pub. No.: WO95/07363

PCT Pub. Date: Mar. 16, 1995

Related U.S. Application Data

[63] Continuation-in-part of Ser. No. 120,066, Sep. 10, 1993, abandoned.

[51] Int. Cl.$^6$ .......................... C12Q 1/68; C07H 21/04; C07H 21/02
[52] U.S. Cl. ...................... 435/6; 935/77; 935/78; 536/24.3
[58] Field of Search .................. 435/6; 935/77, 935/78; 204/182.8; 536/24.3

[56] References Cited

U.S. PATENT DOCUMENTS

| | | | |
|---|---|---|---|
| 4,672,040 | 6/1987 | Josephson | 436/526 |
| 5,059,294 | 10/1991 | Lizardi | 204/182.8 |
| 5,286,434 | 2/1994 | Slater et al. | 204/182.8 |
| 5,356,776 | 10/1994 | Kambara et al. | 435/6 |
| 5,599,664 | 2/1997 | Schwartz | 435/6 |

OTHER PUBLICATIONS

Brandiff et al., "DNA Sequence Mapping by Fluorescence In Situ Hybridization," *Environmental and Molecular Mutagenesis*, 18:259–262 (1991).

Bustamante, "Direct Observation and Manipulation of Single DNA Molecules Using Fluorescence Microscopy," *Ann. Rev. Biophys. Biophys. Chem.*, 20:415–446 (1991).

Dunn et al. "A Novel Method to Map Transcripts: Evidence for Homology between an Adenovirus mRNA and Discrete Multiple Regions of the Viral Genome," 12:23–36 (1977).

Hahnfeldt et al., "Polymer models for interphase chromosomes," *Proc. Natl. Acad. Sci. USA*, 90:7854–7858 (1993).

Lawrence et al., "Interphase and Metaphase Resolution of Different Distances Within the Human Dystrophin Gene," *Science*, 249:928–932 (1990).

Leversha, "FISH and the technicolour revolution," *The Medical Journal of Australia*, 158:545–551 (1993).

Maniatis et al., "Molecular Cloning, A Laboratory Manual," *Cold Spring Harbor Laboratory (N.Y.)* 181, paragraph 4 (1982).

Matthews et al., "Analytical Strategies for the Use of DNA Probes," *Analytical Biochemistry*, 169:1–25 (1988).

Nicholls et al., "Nucleic Acid Analysis by Sandwich Hybridization," *Journal of Clinical Laboratory Analysis*, 3:122–135 (1989).

Ried et al., "Simultaneous visualization of seven different DNA probes by in situ hybridization using combinatorial fluorescence and digital imaging microscopy," *Proc. Natl. Acad. Sci. USA*, 89:1388–1392 (1992).

Saiki et al., "Genetic analysis of amplified DNA with immobilized sequence–specific oligonucleotide probes," *Proc. Natl. Acad. Sci. USA*, 86:6230–6234 (1989).

Smith et al., "Observation of Individual DNA Molecules Undergoing Gel Electrophoresis," *Science*, 243:203–206 (1989).

Smith et al., "Direct Mechanical Measurements of the Elasticity of Single DNA Molecules by Using Magnetic Beads," *Science*, 258:1122–1126 (1992).

Smith et al., "Electrophoretic Charge Density and Persistence Length of DNA as Measured by Fluorescence Microscopy," *Biopolymers*, 29:1167–1173 (1990).

Southern, "Detection of Specific Sequences Among DNA Fragments Separated by Gel Electrophoresis," *J. Mol. Biol.*, 98:503–517 (1975).

Trask, "Fluorescence in situ hybridization," *TIG*, 7:149–154 (1991).

van den Engh et al., "Estimating Genomic Distance from DNA Sequence Location in Cell Nuclei by a Random Walk Model," *Science*, 257:1410–1412 (1992).

*Primary Examiner*—Stephanie W. Zitomer
*Attorney, Agent, or Firm*—Skjerven, Morrill, MacPherson, Franklin & Friel, LLP; Laura Terlizzi; Emily M. Haliday

[57] ABSTRACT

A method for analyzing a sample oligonucleotide sequence is described. The method comprises contacting the sample oligonucleotide sequence with an anchor sequence which comprises an immobilized oligonucleotide sequence which hybridizes with the sample. The sample is also contacted with a probe comprising an oligonucleotide sequence which hybridizes to a target oligonucleotide sequence to be detected in a suitable buffer to form a complex. The complex is subjected to a field which moves unbound oligonucleotide sequences away from the anchor sequence in the direction of the field, and preferably, extends the sample sequence. Whether the probe is bound to the sample oligonucleotide sequence, and preferably, the position of the probe, is determined to determine whether the target oligonucleotide sequence is present in the sample. The method can be used for mapping, for identity typing, and to determine whether a test oligonucleotide sequence is present in the sample. A device for performing the method and reagents are also described.

30 Claims, 3 Drawing Sheets

OPTICAL DETECTION OF POSITION OF OLIGONUCLEOTIDES ON LARGE DNA MOLECULES

The present application is the United States national phase application of PCT/US94/09764, filed Sep. 8, 1994, which is a continuation in part of U.S. application Ser. No. 08/120,006, filed Sep. 10, 1993, now abandoned.

FIELD OF THE INVENTION

The present invention relates to analysis of DNA sequences and, in particular, to optically determining the position of an oligonucleotide sequence on a large DNA molecule.

BACKGROUND OF THE INVENTION

There have been significant advances in DNA analysis methods in recent years. At present, there are several distinct methods for DNA analysis. There are several methods which involve use of an oligonucleotide sequence as a probe to bind to a complementary oligonucleotide sequence which may be present in the sample. This method takes many embodiments from fluorescent in situ hybridization of chromosomes in tissue sections to dot blot analysis of DNA fragments.

The are several DNA analysis methods which involve amplification, usually using the polymerase chain reaction method. In that method, primer, usually on the order of 20 to 30 nucleotides, are used to amplify a region of DNA as large as a few kilobases. The amplified region can be analyzed by a number of methods, including use of probes or sequencing. Alternatively, analyses can be based on the pattern of fragments produced in the amplification.

In addition, DNA can be digested with a restriction endonuclease and the fragment patterns produced can be analyzed to determine alleles present in the sample DNA. Numerous additional methods are used in mapping and cloning to try to identity the location of a gene or to determine which variant of a known gene is present in a sample. All of these analysis methods have advantages and disadvantages and additional, more informative methods are still being sought.

SUMMARY OF THE INVENTION

The present invention provides a method for analyzing a sample oligonucleotide sequence. The method comprises contacting the sample oligonucleotide sequence with an anchor sequence which comprises an oligonucleotide sequence which is immobilized to a support and which hybridizes with the sample oligonucleotide sequence. The sample oligonucleotide sequence is also contacted with a probe comprising an oligonucleotide sequence which hybridizes to a target oligonucleotide sequence to be detected. The contacting is performed in a suitable buffer to form a complex. The resultant complex is subjected to a field which moves unbound oligonucleotide sequences away from the anchor sequence in the direction of the field. Whether the probe is bound to the sample oligonucleotide sequence is determined to determine whether the target oligonucleotide sequence is present in the sample oligonucleotide sequence. Preferably, the complex is subjected to the field for a time sufficient to extend the sample oligonucleotide sequence and the position of the probe in relation to the anchor sequence is also determined.

The field can be a magnetic or, preferably, an electric field in which the oligonucleotide sequences migrate based on their inherent charges. Preferably, the probe is labeled with a fluorochrome, preferably a fluorochrome which is present in a bead, which facilitates use of a fluorescent microscope to determine the presence or position of the probe on the sample oligonucleotide sequence.

In one embodiment, the method is used for mapping. The method can determine whether a first and a second target are on a molecule of sample DNA by having the anchor sequence hybridize to the first oligonucleotide sequence and the probe hybridize to the second oligonucleotide sequence. Alternatively, the nucleotide sequence near the end of the sample DNA molecule to be mapped can be determined using short probes of random sequences, identifying a pair of probes which hybridize toward the end of the sample DNA molecule, and using one probe and the complement of the other to amplify the segment between the probes by the polymerase chain reaction. The nucleotide sequence of this segment can then be determined, and one of the strands from this amplified segment can then be used as a new anchor sequence, to walk down the DNA molecule.

In another embodiment, sample DNA is characterized (fingerprinted) using an anchor sequence which hybridizes to a conserved region in the sample DNA and a plurality of probes of random or arbitrary sequence of from about 5 to about 15 bases. Following hybridization, the sample DNA is extended and unbound probes are removed by the field. The positions of the probes in relation to the anchor sequence are determined. The method can be used in paternity and other forensic applications by using the same anchor and probes on the mother and putative father's DNA or crime scene and suspect DNA.

In another embodiment, the method can be used to determine whether a test oligonucleotide sequence is present in the sample oligonucleotide sequence. In that embodiment, the anchor sequence comprises an immobilized, conserved oligonucleotide sequence known to hybridize with an oligonucleotide sequence in the sample oligonucleotide sequence and the probe hybridizes with the test oligonucleotide sequence. The test oligonucleotide sequence can be any oligonucleotide sequence of interest, such as, for example, a sequence characteristic of a disease gene allele. In a preferred embodiment, a plurality of different probes which bind to different test sequences are used. Each of the probes is labeled with a different fluorochrome or combination of fluorochromes.

A device for performing the method and reagents are also described.

DESCRIPTION OF THE INVENTION

Figure 1:
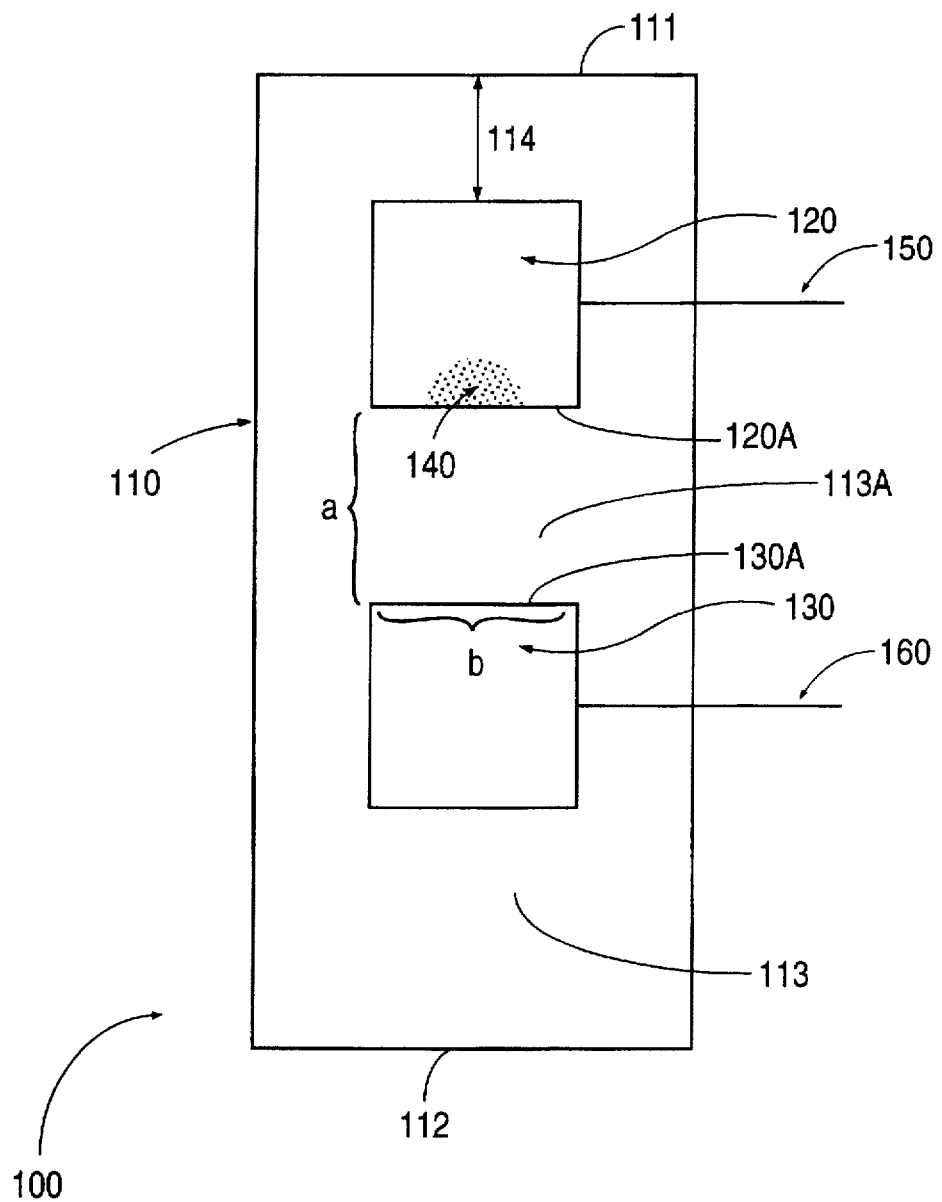
FIG. 1 illustrates a top view of one embodiment of a DNA analysis device of this invention, prior to attachment of a cover.

The present invention provides a method of analyzing oligonucleotide sequences in which the sample oligonucleotide sequence is contacted with an anchor sequence and a probe in a suitable buffer for hybridization. The anchor sequence is an oligonucleotide sequence immobilized to a support which hybridizes with a conserved oligonucleotide sequence present in the sample oligonucleotide sequence. The probe can be any oligonucleotide sequence of interest depending on the type of analysis to be performed. Following formation of a complex by hybridization of the sample oligonucleotide sequence to the anchor sequence, the oligonucleotide sequences are subjected to a field which moves unbound probes away from the anchor sequence. The field preferably also extends the complexed sample oligonucleotide sequence in the direction of the field, thereby facilitating determining the distance between the anchor sequence and the probe and thus the relative positions of the sequences to which the probe and anchor sequence bind. In a preferred embodiment, the probes are labeled with a fluorochrome, facilitating determining distances to within about forty nucleotides using a fluorescent microscope.

In one embodiment, the method can be used for mapping by determining whether two oligonucleotide sequences are on the same molecule of DNA and the distance and direction of the sequences. In another embodiment, the method can be used to characterize DNA sequences and to determine either whether sample and test DNA are from the same individual or whether a putative father can be the father of a child. In another embodiment, sample DNA can be analyzed to determine whether one or a plurality of oligonucleotide sequences, such as oligonucleotide sequences characteristic of a disease gene, are present. A device and reagents facilitating the method are also described.

Reagents and Device for Practicing the Method

The reagents and device used to practice the method of this invention are described below, followed by a description of the method.

The Sample Oligonucleotide Sequence

The sample oligonucleotide sequence can be any oligonucleotide sequence. The present invention is particularly advantageous in analyzing long oligonucleotide sequences; e.g., greater than sizes which can be readily analyzed by polymerase chain reaction methods (2–3 kilobases). The sample oligonucleotide sequence can be DNA or RNA and can be single-stranded or double-stranded. Conveniently, the sample is a single-stranded oligonucleotide sequence, preferably a DNA sequence. However, the method can be performed wherein either the sample oligonucleotide sequence or the anchor sequence is double-stranded and the complex formed by hybridization is a triple helix. The binding rules for triple helix formation are well known and are described in International Application No. PCT/US89/05769 (Publication No. WO 90/06934, published Jun. 28, 1990) to Hogan et al., for example. That application is incorporated herein by reference in its entirety.

Extraction of sample oligonucleotide sequences from cells and preparation of single-stranded oligonucleotide sequences are well known. All nucleated cells contain genomic DNA and RNA and, therefore, are potential sources of the sample oligonucleotide sequence. For higher animals, peripheral blood cells are typically used rather than tissue samples. As little as 0.01 to 0.05 cc of peripheral blood provides sufficient DNA for analysis. Hair, semen and tissue can also be used as samples. In the case of fetal analyses, placental cells or fetal cells present in amniotic fluid can be used. When the sample oligonucleotide sequence is DNA, the DNA is isolated from nucleated cells under conditions that minimize DNA degradation. Typically, the isolation involves digesting the cells with a protease that does not attack DNA at a temperature and pH that reduces the likelihood of DNase activity. For peripheral blood cells, lysing the cells with a hypotonic solution (water) is sufficient to release the DNA. Generally, red white blood cells which do not contain nuclei are separated from the nucleated white blood cells prior to extraction of DNA.

DNA isolation from nucleated cells is described by Kan et al., *N. Engl. J. Med.* 297:1080–1084 (1977); Kan et al., *Nature* 251:392—392 (1974); Kan et al., PNAS 75:5631–5635 (1978); and in Sections 2.1 and 2.2 of Ausubel, Short Protocols in Molecular Biology, Second Edition, John Wiley and Sons, New York (1992). In addition, commercial DNA purification kits are available. (See page 190–191 in BioRad Laboratories: BioRad Laboratories Catalog: Life Science Research Products, Hercules, Calif., Bio-Rad Laboratories (1993) which describes the InstaGene DNA purification kit.) Each of the above references is incorporated herein by reference in its entirety. Extraction procedures for samples such as blood, semen, hair follicles, semen, mucous membrane epithelium and other sources of genomic DNA are well known. For plant cells, digestion of the cells with cellulase releases DNA. Thereafter DNA is purified as described above.

Procedures for isolating RNA from cells are described in Sections 4.1 and 4.2 of Ausubel, Short Protocols in Molecular Biology, Second Edition, John Wiley and Sons, New York (1992) and pages 38 to 50 of Pharmacia Corporation: Pharmacia Catalog: Molecular and Cell Biology, Pharmacia Corporation, 1993.

The extracted oligonucleotide sequence can be purified by dialysis, chromatography, or other known methods for purifying oligonucleotides prior to analysis. Typically, the oligonucleotide sequence is not purified prior to analysis by the methods of this invention. However, usually, RNA in the sample is digested when the sample oligonucleotide sequence is DNA, and DNA is digested when the sample oligonucleotide sequence is RNA.

The method can be performed on a sample oligonucleotide sequence which is less than about 200 kb using normal handling techniques in preparing the sample oligonucleotide sequence. However, when the sample oligonucleotide sequence is greater than about the size of T4 DNA (greater than about 200 kb), special handling techniques are used in preparing the sample oligonucleotide sequence.

The techniques for handling long oligonucleotide sequences are well known and involve processing techniques which minimize forces which can shear oligonucleotide sequences. For example, cells containing the sample oligonucleotide sequence can be lysed in a gel to preserve the integrity of the oligonucleotide sequences. The gel is usually a gel which is solid at room temperature and liquid at an elevated temperature such as 37° C. For example, on page 84 in Promega Corporation: Catalogue: Biological Research Products, Madison, Wis., Promega Corporation, (1992–3) describes preparation of intact yeast chromosomes from whole cells embedded in 0.8% low melt point agarose. The cells are lysed and deproteinized in situ as described in McClelland et al., *Nucl. Acid Res.* 15:5985 (1987).

A fragment of the gel is removed for analysis to avoid pipetting, mixing, and other techniques which exert shear forces. The reagents for the analysis method are allowed to diffuse into the gel to achieve the desired effects on the cells containing the DNA or the DNA itself. When using such samples, the analysis procedure is performed at an elevated temperature at which the gel is liquid.

When the sample oligonucleotide sequence is DNA, preferably, the DNA strands are separated into single stranded DNA prior to analysis. This strand separation can be accomplished by a number of methods including physical or chemical means. A preferred method is the physical method of separating the strands by heating the DNA until it is substantially (approximately 93%) denatured. Heat denaturation involves temperatures ranging from about 80° to 105° C. for times ranging from about 15 to 30 seconds. Typically, heating the DNA to a temperature of from 90° to 93° C. for about 30 seconds to about 1 minute is sufficient. Alternatively, sample oligonucleotide sequences can be denatured by heating at 75° C. for 5 minutes in 70% formamide (final concentration), 0.3M NaCl, 0.01M Tris-HCl, pH 8.5, 0.001M EDTA.

The Anchor Sequence

The anchor sequence is an oligonucleotide sequence immobilized to a support which hybridizes with a conserved oligonucleotide sequence present in the sample oligonucleotide sequence. The anchor sequence is also unique in the total oligonucleotide population the sample oligonucleotide has been obtained from; e.g. human genomic DNA. The anchor sequence can be any oligonucleotide sequence which hybridizes to the sample sequence, forming a complex which is sufficient to immobilize the sample oligonucleotide sequence in the presence of an electric field that removes unbound probes. Preferably, the anchor sequence forms a complex which is sufficient to immobilize the sample oligonucleotide sequence in the presence of an electric or magnetic field that extends or elongates the sample oligonucleotide sequence in the direction of the field, thereby facilitating determining the distance of the probe from the anchor sequence.

The anchor sequence can be a DNA sequence or an RNA sequence. The anchor sequence is preferably a single-stranded oligonucleotide sequence to provide sufficient binding to immobilize the sample oligonucleotide sequence in the electric field. However, double-stranded oligonucleotide sequence which hybridizes to a single-stranded sample oligonucleotide sequence to form a triple helix are also contemplated. In addition, the use of a peptide nucleic acid oligomer sequence which can displace one strand of a double helix to hybridize to the sequence on the second strand is contemplated (see Peffer et al., *Proc. Natl. Acad. Sci. USA* 90:10648–10652 (1993)).

The anchor sequence is preferably a conserved oligonucleotide sequence to ensure that the sample sequence contains a sequence which hybridizes to the anchor sequence. In addition, the anchor sequence is sufficiently long to ensure that the sequence is unique. Such considerations are well known and are substantially the same considerations used in selecting a probe for various techniques, such as for in situ hybridization (ISH).

When distances between the anchor sequence and probe are to be determined, the anchor sequence is sufficiently long and sufficiently complementary to the target sequence in the sample oligonucleotide sequence to ensure that the sample oligonucleotide sequence remains hybridized to the anchor sequence in the presence of the field used to extend the sample oligonucleotide sequence. Preferably the anchor sequence is from about 10 to about 100 bases, preferably from about 20 to about 40 bases, most preferably about 30 bases.

As the length of the anchor sequence increases, the degree of specificity for a unique sequence increases. In addition, the strength of the bonds formed by hybridization increases as the length of the anchor sequence increases, providing the sample oligonucleotide sequence/anchor sequence complex with the ability to remain a complex and thus immobilized in a stronger field. However, longer oligonucleotide sequences are more difficult and expensive to prepare than shorter oligonucleotide sequences. Therefore, these conflicting interests are balanced in selecting the length of the anchor sequence.

As in ISH applications, the anchor sequence need not be the Watson Crick complementary sequence to the target sequence on the sample oligonucleotide sequence so long as the binding between the anchor sequence and the sample oligonucleotide sequence is sufficient to immobilize the sample oligonucleotide sequence, as stated above. However, the anchor sequence is preferably complementary to the target oligonucleotide sequence in the sample oligonucleotide sequence to optimize the ability of the sample oligonucleotide sequence/anchor sequence complex to remain complexed when subjected to the field.

Methods for selecting and synthesizing such oligonucleotide sequences are well known. In addition, considerations for selecting anchor sequences for particular applications are described in detail hereinafter.

The anchor sequence can be bound to the support either directly or through a linking group by any of the methods described hereinafter. The linking group can be an irrelevant oligonucleotide sequence which allows the anchor sequence to extend from the surface of the support to facilitate binding of the entire anchor sequence to a sample oligonucleotide sequence. Such irrelevant oligonucleotide sequences are preferably sequences which are flexible and can bend, such as for example, poly-T having at least three nucleotides, preferably at least 5 nucleotides.

Alternatively, the linking group can be a polypeptide, preferably a relatively short polypeptide. Methods for linking peptides or proteins to nucleic acids and to the solid phase are discussed above. The peptide linker is preferably from four to twenty, preferably from five to 10, amino acid residues in length. The peptide does not include with a large number of positively charged groups to avoid non-specific binding of oligonucleotide. The peptide preferably also does not have a large number of negative charges to facilitate binding to the anchor sequence. Preferably the peptide does not include very hydrophobic amino acids, such as leucine, because leucine is relatively insoluble, thus difficult to work with, and might bind to the surface of the polystyrene bead. A polypeptide with one amino group at one end and one carboxyl group at the other is preferred. Homopolymers are preferred.

Most preferred linkers are polyglycine, polyalanine, and polyproline. Polyalanine forms an alpha helix which would hold the anchor sequence away from the support surface or, when linking the probe to the label, would hold the probe oligonucleotide sequence out from the bead. Polyproline forms a rigid coil (not an alpha helix), which can also be used to hold the oligonucleotide sequence out from bead or support. In addition, a large variety of other small organic molecules can also be used.

The anchor can be linked to the solid support at an internal oligonucleotide in the anchor sequence, so that there are two "arms" of the anchor sequence hanging from the linker. A restriction site near the end of one of the arms then provides a means for cutting that arm off. DNA with a linker site anywhere in the sequence is available commercially from; e.g., The Midland Certified Reagent Company (Midland, Tex.) and Peninsula Laboratories (Belmont, Calif.).

The support to which the anchor sequence is immobilized can be any solid phase on which hybridization can be performed. The solid phase is preferably a glass or plastic surface, conveniently a microscope slide. For use with an epifluorescent microscope, the slide is preferably opaque to absorb light which may otherwise be reflected. A preferred support is described hereinafter in describing a preferred device of this invention.

The anchor sequence is bound to the support by conventional methods. The goal of the surface chemistry is to attach a few sample oligonucleotide sequence DNA to the support through hybridization with the anchor sequence, as it is necessary to observe only a few molecules. Thus, the chemistry need not be very efficient. This is in contrast to the requirements in, for example, procedures for solid support DNA synthesis machines, where the goal is to produce as much product as possible. Therefore, a number of techniques are suitable.

For example, to attach the anchor sequence to the support, a portion of the support is coated with a solution of gelatin, which is then allowed to dry into a film coating the surface of the support. The gelatin is then crosslinked to make it irreversibly insoluble using standard techniques of histological specimen preparation. Such techniques are well known and are described in Galigher and Kozloff, *Essentials of Practical Microtechnique*, Lea & Febiger, Philadelphia, (1964) for example. Activated anchor oligonucleotides are then covalently attached at the free amino groups of the gelatin.

Alternatively, methods used for synthesis of DNA involve a solid, silica-based (e.g., glass) support, having the 3' nucleotide covalently linked to the support. This linkage is accomplished by reacting the nucleotide 3'-p-nitrophenylsuccinate ester with a free amino group on the surface of the support. (See Caruthers, *Science* 230:281–285 (1985) for a review of automated oligonucleotide synthesis methods.) The method can also be used to attach the anchor sequence to a glass or other silica-based support.

For RNA anchor sequences, the anchor sequence can also be linked by either the 2' or 3' hydroxyl on ribose by well known chemistry.

Alternatively, a metal, such as gold, silver, or copper, can be attached to the support and used to bind the anchor sequence to the support. Conveniently, the metal can also function as the electrode. There are numerous articles on the reaction of thiols with gold, silver, and copper surfaces which can be used to attach the anchor sequence to the metal and thus to the support. (See for example, Laibinis et al., *J. Am. Chem. Soc.* 114:1990–1995 (1992).)

In addition, Whitesell et al., *Science* 261:73–76 (1993) describe the preparation of a gold surface which has been deposited by evaporation onto glass. The gold surface is coated with an aminotrithiol "tripod". The three thiol groups bind tightly to the gold surface, and the amino groups are exposed at the opposite, free surface. Although the authors describe linking polypeptides to the free amino groups, nucleotides could also be attached, using the chemistry described previously. Bifunctional organic disulfides also bind tightly to gold surfaces. (See for example Nuzzo et al., *J. Am. Chem. Soc.* 105:4481–4483 (1983).)

Using a metal surface is advantageous because the metal surface can also be used as an electrode to produce an electric field. Gold is preferred because it is generally chemically inert. In addition, fabrication of micro patterns of gold films, used in the computer chip industry, is well known and is commercially available. However, with many electrolytes, gas is evolved at the electrode surface, and may interfere with observation. Thus, it may be advantageous to use an alternating high frequency electric field to extend the DNA (see Kabata et al., *Science* 262:1561–1563 (1993)), since no gas is evolved when there is no net current.

Photoresist fabrication techniques can also be used to produce patterns of methylsilane and aminosilane on the surface of glass. (See Britland et al., *Biotech Prog.* 8:155–160 (1992).) The methylsilane produces a non-reactive surface, while peptides and proteins (and nucleotides) can be coupled to the aminosilane surface using chemistry described above when the anchor sequence is linked to a peptide.

The Probe

A probe of this invention is an oligonucleotide sequence which hybridizes to a target region of the sample oligonucleotide sequence. As with the anchor sequence, the probe can be a DNA sequence or an RNA sequence is preferably single-stranded to maximize the strength of the bond between the probe and the sample oligonucleotide sequence.

As with the anchor sequence, the probe can hybridize with the target sequence in the sample oligonucleotide sequence by Watson Crick or triple helix binding. However, use of a single stranded probe and sample oligonucleotide sequence was preferred. The same general considerations regarding the percentage and location of complementary oligonucleotides are involved for the probe as for the anchor sequence. However, when the sample oligonucleotide sequence is extended and the probe is separated from the hybridization mixture by an electrical field, the probe need not be as tightly bound to the sample oligonucleotide sequence as the anchor sequence. The anchor sequence experiences the force of the electric field acting on the entire length of the sample sequence. The probe only experiences the force on the length of the probe. Therefore, a relatively short probe can be used and remain bound (hybridized) in a field which requires a substantially longer anchor sequence for the anchor sequence to remain hybridized.

If the probe is attached to a magnetic particle, the considerations would be the same as for an anchor sequence which hybridizes to a sample oligonucleotide sequence which is bound to the magnetic particle. That is, the probe would need to be the same length as an anchor sequence attached to a particle of the same magnetic field strength. However, to use shorter probes, a particle having a lower magnetic field strength can be used. Thus, the same size probes can be used whether the separation means is a magnetic or electric field.

The length of the probe on the target region of the sample oligonucleotide sequence to which the probe binds depends on the analysis to be performed. In general, the criteria for selection of probe length and target sequence do not differ from those of the prior art, with the exceptions described above for use of magnetic particle-labeled probes. For example, general considerations for selection of appropriate probes are usually those used for selection of probes for fluorescent in situ hybridization (FISH) methods. FISH is a technique used to detect, quantitate and localize RNA and DNA in cells and tissues, usually in fresh frozen or paraffin-embedded tissue sections. In FISH methods, a fluorochrome-labeled probe oligonucleotide sequence is incubated with the tissue section to hybridize the probe to a sample oligonucleotide sequence.

When one wants to determine whether two oligonucleotide sequences are on the same molecule of DNA, such as for mapping applications, the anchor sequence is selected to bind to the first oligonucleotide sequence and the probe is selected to bind to the second oligonucleotide sequence.

Considerations for selection of oligonucleotide sequence for such probes does not differ from those for probes for in situ hybridization techniques and are well known. The probes can be any sequence which hybridizes specifically to the second oligonucleotide sequence under the conditions for the method. The probes are preferably from about 10 to about 100 bases, preferably from about 20 to about 40 bases, most preferably about 30 bases.

For preparing characteristic patterns for sample DNA for identity typing applications, such as in forensics or paternity determinations, the present invention uses relatively short oligonucleotide sequences, on the order of about 5 to 15, usually 7 to 10, nucleotides of arbitrary sequence. Such oligonucleotide sequences can be selected to bind approximately every 1,000 (for probes of 5 bases) to 1,000,000,000 (for probes of 15 bases) bases of genomic DNA, depending on the length of the probe sequence. An arbitrary nucleotide sequence of 6 bases binds once approximately every 4,000 bases, and a probe of 10 nucleotides binds once approximately every 1,000,000 nucleotides. Most preferred are probes of 7 or 8 nucleotides of arbitrary sequence.

However, if binding every 4,000 nucleotides is desired and a probe of six nucleotides is not sufficiently long to remain hybridized during the analysis, the probe can be effectively made ten nucleotides in length while retaining the same specificity by synthesizing a plurality of probes. The probes each have the selected six nucleotides. The probe is elongated by making four versions of the probe at each of the remaining four positions to produce a probe ten nucleotides in length. That is, 256 probes of different specificity, each with the same six nucleotides and every combination of nucleotides at the remaining four positions can be synthesized. Of course, the concentration of the probes would have to be increase 256-fold in this example to maintain the same molarity of the specific probe for efficient hybridization. See page 6.9 in Ausubel, Short Protocols in Molecular Biology, Second Edition, John Wiley and Sons, New York (1992). In this way, the desired frequency of binding can be achieved while maintaining a sufficient strength of binding to remain hybridized during the analysis.

Selection of such oligonucleotide sequences for use as primers is well known and is described in International Application No. PCT/US91/00841 (Publication No. WO 91/14001, published Sep. 19, 1991) to Livak et al., (the RAPD method), for example.

When the probe is to hybridize with a target sequence of interest, such as an oligonucleotide sequence characteristic of a disease gene, the probe is generally at least about 15, preferably at least about 20 nucleotides to ensure the desired specificity. The probe sequence is preferably 10 to about 100 bases, preferably from about 20 to about 40 bases, most preferably about 30 bases. Probes of about 20 to about 30 nucleotides can be selected to be specific to a target oligonucleotide sequence and are readily synthesized.

In addition, the probes are labeled with a fluorochrome. The fluorochrome provides essentially a point source of light which facilitates detection of the probes on the sample oligonucleotide sequence. Fluorochromes are well known and include fluorescein (e.g., fluorescein isothiocyanate—FITC), rhodamine (e.g., tetramethylrhodamine isothiocyanate—TRITC), phycoerythrin (PE), allophycocyanin (APC) and Texas Red (Molecular Probes, Eugene, Oreg.).

A most preferred fluorescent label is a fluorochrome incorporated into a plastic bead, preferably a polystyrene bead of controlled diameter. The fluorochrome is incorporated into a plastic bead during the manufacture of the beads to avoid having the dye molecules to leach away from the bead during the incorporation process. The fluorochromes are protected from the photobleaching that plagues conventional FISH methods, since oxygen and oxygen radicals cannot readily reach the dye molecules. The spheres can contain many molecules of fluorochrome, providing a bright image which is readily detectable and is particularly advantageous for image analysis techniques.

Fluorochrome-containing polystyrene spheres can be purchased from Duke Scientific Corporation (Palo Alto, Calif.). Green, red, and blue fluorochrome-containing spheres 0.5 microns in diameter are available with reagents that covalently link peptides to the plastic. In particular, beads that can be linked to carboxyl groups on peptides are commercially available under the tradename FX COVASPHERES from Duke Scientific Corporation. Beads of other, smaller and larger diameters are also commercially available.

Techniques for binding a fluorochrome to an oligonucleotide sequence are well known and are utilized in fluorescent in situ hybridization techniques. As stated previously, in FISH methods, a fluorochrome-labeled probe oligonucleotide sequence is incubated with the tissue section to hybridize the probe to a sample oligonucleotide sequence.

The probes are typically labeled with a fluorochrome using one of three techniques. In a first technique, the probe is conjugated to the fluorochrome. See, for example, Bauman et al., in Flow Cytogenetics, J. W. Grey Editor, Academic Press, London, 1989, and which describes methods for binding fluorochromes to oligonucleotide sequences.

In a second method, the probe has a biotin covalently attached to one or more nucleotides. The sample oligonucleotide sequence is contacted with avidin which has been labeled with a fluorochrome. Avidin binds tightly to biotin, and thus the probe is labeled. The hybridization of probe and sample can be performed simultaneously with contacting the probe with avidin. Alternatively, the hybridization of probe and sample can be performed as a first step, and incubation with the avidin is done following hybridization. The separation of steps is particularly useful when the hybridization conditions are sufficiently harsh that the avidin could be denatured and inactivated.

In the third technique, the probe has digoxigenin covalently attached to one or more nucleotides, and a fluorochrome-labeled anti-digoxigenin, antibody binds the digoxigenin. This procedure is analogous to the biotin/avidin procedure described above. Digoxigenin is used because extremely high affinity anti-digoxigenin antibodies are commercially available.

FISH techniques are within the level of skill in the art and are reviewed in Leversha, *Med. J. Australia* 158:545–551 (1993). Other articles describing FISH techniques include Trask, *TIG* 7:149–154 (1991); Brandriff et al., *Envirn. Mol. Mutagen* 18:259–262 (1991); Bauman et al., In: Gray JW, eds. Flow Cytogenetics, London: Academic Press, 275–301 (1989); Pinkel et al., *Proc. Natl. Acad. Sci. USA* 83:2934–2938 (1986); and Pinkel et al., *Proc. Natl. Acad. Sci. USA* 85:9138–9142 (1988). Specific laboratory directions for in situ hybridization, exemplified by detection of cellular RNA using radioactive probes, are given on pages 14-2 to 14-19 of Ausubel, Short Protocols in Molecular Biology, Second Edition, John Wiley and Sons, New York (1992).

In a preferred labeled probe construct, one end of a polypeptide spacer is bound to the probe, and the other end of the spacer is bound to a fluorescent bead. Preferably, the amino terminus of a polypeptide spacer is covalently bound to the probe, and the carboxy terminus is covalently bound to the fluorescent bead. The peptide spacer can be bound to any portion of the probe. However, when the bead has a large negative charge, the bead is preferably attached at the end of the probe distal to the anchor, so that the force of the electric field is distributed along the length of the probe, rather than experienced by the nucleotides at the proximal end of the probe, and thus removed from the sample DNA.

The spacers can be the same as the anchor sequence linking sequences described above. A preferred polypeptide spacer is polyglycine, having from four to twenty, preferably from five to 10 glycines. Oligonucleotides that can be coupled to free amino groups are commercially available. Such oligonucleotides are readily coupled to the amino group of a linker peptide which has been coupled to the bead.

In applications where a plurality of probes are used to bind to a plurality of target regions in the sample oligonucleotide sequence, each probe can be labeled with a different fluorochrome. Combinations of fluorochromes used for labeling are chosen so that distinguishable wavelengths of light are emitted. For example, use of three different fluorochromes of distinguishable colors facilitates the identification of seven different probes. (See Ried et al., *Proc. Natl. Acad. Sci. USA* 89:1388–1392 (1992) which describes the identification of seven different probes using three fluorochromes in a fluorescent in situ hybridization method.)

By controlling the intensity of the light emitted by each of the fluorescent plastic beads, different intensity levels can also be measured, distinguishing probes with one bead from those with two or more beads. Together with use of different colors, large numbers of different probes can be distinguished. The intensity of light emitted at different wavelengths by different types of beads is determined by the total amount of the relevant fluorochrome in the bead.

The Device

A DNA analysis device 100 of this invention has a generally planar support 110 having a first end 111 and a second end 112 which is opposite to, removed from, and substantially parallel to first end 111. Support 110 can be glass or plastic, and is conveniently a microscope slide. Support 110 can be transparent or opaque. The support is preferably opaque when used with an epifluorescent microscope.

A first electrode 120 is preferably fixedly attached to a planar surface 113 of support 110 adjacent to but separated from first end 111 of support 110. A second electrode 120 is preferably fixedly attached to planar surface 113 of support 110 adjacent to but separated from second end 112 of support 110. The spacings of first and second electrodes 120, 130 from first and second ends 111, 112, respectively, is not critical. The important aspect as explained more completely below is the spacing between electrodes 120, 130.

Electrodes 120, 130 are made of an electrically conductive material, preferably copper, silver, or more preferably, gold. In one embodiment, electrodes 120, 130 are small rectangles, on the order of 5×5 mm which are formed from thin, flat sheets, e.g., a foil, of the selected metal. First and second electrodes 120, 130 have approximately the same thickness. The anchor sequence is immobilized on support 110 adjacent first electrode 120, and, preferably, on first electrode 120. The anchor sequence is immobilized on first electrode 120 in region 140, i.e, a middle region of electrode 120, and extends toward a portion 113A of surface 113.

To attach the anchor sequence to first electrode 120, at least a portion 140 of electrode 120 which is exposed to an interior of device 100, conveniently the entire electrode, is coated with a solution of gelatin, which is then allowed to dry into a film coating the surface of electrode 120. The gelatin is then crosslinked and attached to the anchor sequence as described previously. Alternatively, electrode 120 can be coated with an aminotrithiol and the anchor oligonucleotides are then attached as described above. Following attachment of the anchor sequence or a linking group, first electrode 120 is attached to surface 113 of support 110 by glue such as an epoxy adhesive. Second electrode 130 is also attached to surface 113 by glue.

A substantially planar cover (not shown in FIG. 1 for clarity) extends at least from first electrode 120 to second electrode 130. The cover is preferably transparent for most uses but can be opaque when used with an inverted epifluorescent microscope. In one embodiment, the cover rests on electrodes 120, 130. In another embodiment, the cover is attached to electrodes 120, 130 by glue. The cover can be glass or plastic or any other transparent material. Conveniently, the cover is a conventional microscope coverslip.

Placing the cover on electrodes 120, 130 forms a detection chamber bounded by edges 120A and 130A of electrodes 120 and 130, respectively; a portion 113A of surface 113 between electrodes 123; and the surface of the cover between electrodes 120 and 130. The detection chamber has a size of h×a×b, where a and b are preferably on the order of 10 mm each and h is preferably on the order of one millimeter. One of the remaining sides of the detection chamber can be sealed with a material which does not interfere with the hybridization process, preferably small strips of glass or plastic which can be positioned after addition of the hybridization reagents. Alternatively, the detection chamber can be sealed on one or both of the remaining sides with rubber cement. Device 100 is preferably supplied with the anchor oligonucleotides attached, preferably in a desiccated container to avoid possible degradation of the anchor oligonucleotide.

First and second electrodes 120, 130 are attached to wires 150 and 160, respectively, for electrical connection to a power supply. Preferably, wires 150 and 160 are each a 28 gauge wire. (28 gauge wire has a 0.65 mm diameter.) Each 28 gauge wire is connected to a separate terminal. Larger wires, which in turn connect to the power supply, are also connected to the terminals.

When a first voltage level is applied to first electrode 120 and a second voltage level, different from the first voltage level, is applied to second electrode 130, an electric field is formed between electrodes 120 and 130 which acts on the anchor sequence as described above.

Figure 2:
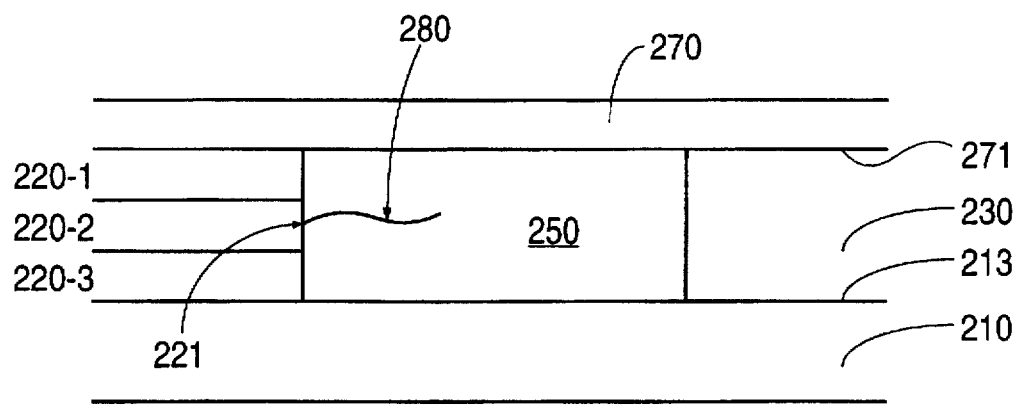
FIG. 2 illustrates a side view of another embodiment of a DNA analysis device of this invention having a composite electrode.

In another embodiment, as illustrated in FIG. 2, first electrode 120 (FIG. 1) is replaced with a composite electrode 220 having three sandwiched electrode layers 220-1, 220-2, and 220-3 that are formed from three sheets of metal. The sheets of metal are conveniently of equal thickness. The thickness of the metal foil is selected so that the thickness of composite electrode 220 is approximately equal to the thickness of second electrode 230.

Prior to assembling composite electrode 220, the anchor sequence, or a linking group which facilitates subsequent attachment of the anchor sequence is bonded to central electrode layer 220-2 in the same manner as described above for first electrode 120 and that description is incorporated herein by reference. After central electrode layer 220-2 is coated, layer 220-2 is sandwiched between electrode layers 220-1 and 220-3 so that electrode layer 220-2 is in the center of composite electrode 220.

First electrode 220 and second electrode 230 are attached adjacent to, but removed from opposite ends of surface 213 of support 210 in a manner similar to that described above for electrodes 120 and 130 of FIG. 1. After attachment to surface 213, first electrode 220 and second electrode 230 are covered by cover 270 to form detection chamber 250. The anchor sequence is only exposed to detection chamber 250 at edge surface 221 of center electrode layer 220-2. Two outside electrode layers 220-1 and 220-2 of composite electrode 220 not only make electrode 220 the same height as second electrode 230 but also restrict the sample oligonucleotide sequence to a central zone of detection chamber 250, while ensuring a uniform, parallel electric field to extend the sample oligonucleotide sequence. Sample oligonucleotide sequence 280 is shown after hybridization of the sample to the anchor sequence.

The depth of field (focus) of a microscope at high power is sufficiently narrow so that one could just focus on a middle zone of composite electrode 220. Any distorted oligonucleotide sequence molecules at the electrode edges would be sufficiently out of focus that so that no interference with observation of molecules with the desired orientation would occur.

Figure 3:
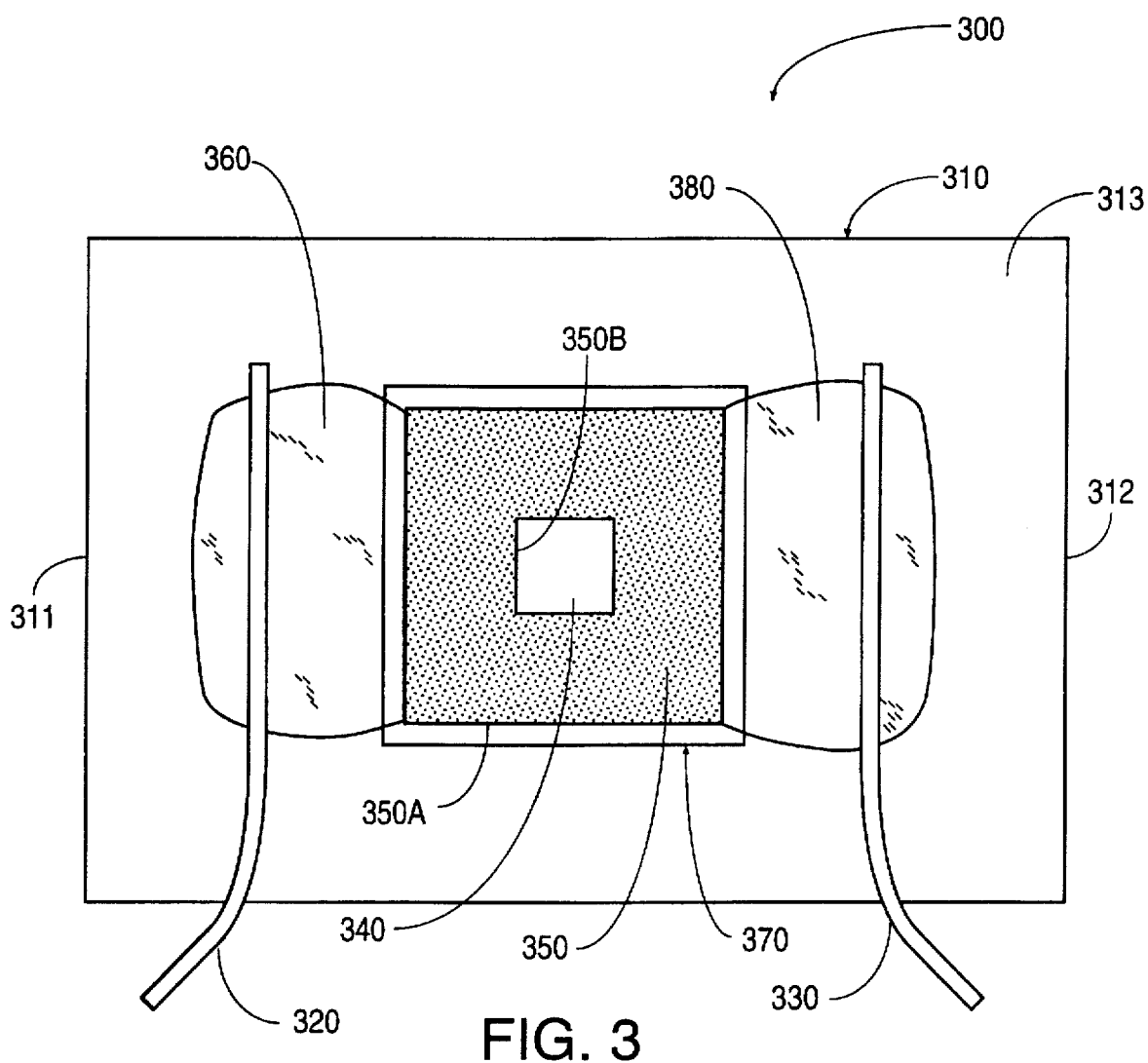
FIG. 3 illustrates a top view of another embodiment of a DNA analysis device of this invention.
Figure 4:
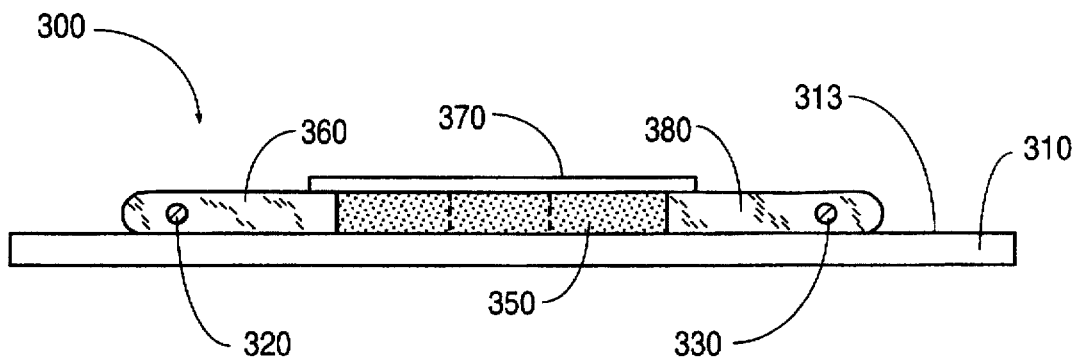
FIG. 4 illustrates a side view of the embodiment of the device illustrated in FIG. 3.

FIGS. 3 and 4 illustrate another embodiment of a DNA analysis device 300 of this invention. Preparation and use of one embodiment of device 300 is described in detail in Example 4. In FIG. 3, support 310, conveniently a large coverslip, has a generally planar surface 313, with a first end 311 and a second end 312 which is opposite to and removed from first end 311. Support 310 is prepared as described in Example 4.

First electrode 320 is placed directly on surface 313 adjacent to but separated from first end 311. Second electrode 330 is placed on surface 313 adjacent to but separated from second end 312 of surface 310. As in the previous embodiments described above, the spacing of electrodes 320 and 330 from ends 311 and 312, respectively, is not critical. First electrode 320 and second electrode 330 are round wire electrodes for electrical connection to a power supply. First and second electrodes 320 and 330 are approximately the same size wire.

In the embodiment described in Example 4, DNA analysis device 300 is mounted on a transparent stable dielectric plastic sheet. The plastic sheet is not shown in FIGS. 3 and 4, because the plastic sheet is not an important feature of the invention. Moreover, dimensions given herein are illustrative only and are not intended to limit the invention to the particular dimensions given. In view of this disclosure, those skilled in the art can implement DNA analysis device 300 in a wide variety of sizes, shapes, and forms.

In the embodiment of Example 4, two brass bolts are passed through two holes, approximately 50 mm apart, in the plastic sheet and nuts attached to the bolts. Electrode 320 is wound around one of the bolts and the nut is tightened against electrode 320. Electrode 320 is wound around the other of the bolts and the nut is tightened against electrode 330. Thus, electrodes 320 and 330 are spaced approximately 50 mm apart. Electrodes 320 and 330, after attachment to the bolts, have some springiness and so support 310 is slid under electrodes 320 and 330, and is held in place by electrodes 320 and 330.

A cavity is formed through a gel to form a gel frame 350 so that gel frame 350 has an exterior surface 350A and an interior surface 350B. Gel frame 350 is made of a material suitable for electrophoresis of nucleic acid, and is preferably made from a polyacrylamide gel sheet of uniform thickness. Although illustrated as a square, the cavity can be of any shape. Generally, the shape of exterior surface 350A is the same as the shape of interior surface 350B. In the embodiment of Example 4, exterior surface 350A is the exterior surface of a 10×10 mm square and interior surface 350B is the surface of a 5×5 mm square. The vertical thickness of gel frame 350 is one millimeter.

Gel frame 350 with the cavity is placed on surface 313 so that a center of the cavity is approximately centered between electrodes 320 and 330, and so that the cavity forms an electrophoresis chamber 340, hereinafter chamber 340, having a bottom surface that is a portion of surface 313 and a vertical surface that is inner surface 350B of gel frame 350. Chamber 340 is filled with a buffer solution (an electrophoresis buffer) containing an anchor oligonucleotide sequence affixed to a solid support, conveniently an agarose ball as described in Example 4 (not shown).

Pools 360 and 380 are drops of a solution that conducts electricity from electrodes 320 and 330, respectively, to gel frame 350. Conveniently, pools 360 and 380 are drops of the electrophoresis buffer used for the DNA analysis in chamber 340.

A cover 370, conveniently a small coverslip, is placed on top of gel frame 350, following loading of an anchor oligonucleotide sequence into chamber 340, to seal chamber 340 by forming a top surface that is opposite and removed from the bottom surface that is a portion of surface 313. Cover 370 can be any solid, material that covers, and thereby seals, chamber 340. Cover 370 is conveniently made of a transparent material to facilitate observation of materials in chamber 340.

FIG. 4 is a side view of DNA analysis device 300 of this invention. First electrode 320 and second electrode 330 are shown in pools 360 and 380, respectively that are formed on planar surface 313 of support 310. Gel frame 350 is covered by cover 370.

The Method

The method is described generally below, followed by various embodiments of the method adapted for particular analysis techniques.

The first step in performing the present method is contacting a sample oligonucleotide sequence with an anchor sequence of this invention and with a probe in a suitable buffer to form a complex between the sample oligonucleotide sequence and the anchor sequence. The sample oligonucleotide sequence and probe can be mixed prior to contact with the anchor sequence, or the sample oligonucleotide sequence can be contacted with the anchor sequence and then the probe can be added to form a hybridization mixture. Following hybridization, unbound probe and, preferably, unbound sample oligonucleotide sequence are removed. Any probe which binds to a sample oligonucleotide sequence which is immobilized to the support through the hybridization to the anchor sequence is then detected.

The conditions for hybridization of oligonucleotide sequences are well known. Generally, the hybridization step is either performed in a buffered aqueous salt solution at high temperature or in the presence of formamide at lower temperature. The aqueous, high temperature procedure is typically carried out in a Tris buffer, such as 0.3M NaCl, 20 mM Tris-HCl, pH 6.8, at 67° C. Other buffering systems such as hepes or glycine-NaOH and potassium phosphate buffers can be used.

One to ten nanograms of the probe is generally used per hybridization mixture. However, when using probes with a lower sensitivity, increased probe concentrations; e.g., 250–750 ng/ml in the hybridization solution. Such high probe concentrations facilitates short hybridization times of about one to two hours.

When the probe is attached to a bead, the size of the bead used is a consideration at high probe concentrations. For example, if the bead is 1 micron in diameter, a concentration of 2 nM would be almost solid beads. 2 nM would be 7 ng/ml for a 10 base probe. If the beads were only 0.1 microns in diameter, a concentration 1000 times higher can be used. Preferably, the beads are from about 0.1 to about 0.2 microns in diameter. Such sizes not only allow use of probes at higher concentrations, but also facilitate faster hybridization, because the diffusion coefficients are higher.

Typically, the total volume of the buffer containing the sample oligonucleotide sequence and probes (the hybridization mixture) required is about 15 to 20 µl. For use in a device of this invention, rather used as a drop placed on a slide or other support, the dimensions of the device determine the required volume. If the device is 1 mm$^3$, the required volume is one µl. Similarly, if the device is 2×5×5 mm, the volume would be 50 µl. A preferred device of this invention having a detection chamber of 1×10×10 mm requires a volume of 100 µl.

When added to the assay device, the hybridization mixture is covered, as with a coverslip or by placing in a sealed device to prevent evaporation of the reagents. Generally, the hybridization step is performed 12 to 14 hours at 37°–42° C. in a chamber humidified with the hybridization buffer.

Alternatively, the hybridization is performed in formamide at lower temperatures. The formamide procedure is generally used with thermally sensitive probes. For example, biotinylated probes are less thermally stable than radioactive probes. With such probes, the formamide concentration is generally lowered from about 50 to about 45% in otherwise standard in situ hybridization conditions. Typically, the hybridization is carried out in about 40% to 50% formamide in SSC (0.15M NaCl, 0.015 trisodium citrate, pH 7.0 (adjusted with NaOH). The probe and carrier DNA or RNA concentrations are the same as for the aqueous buffer solution. A preferred formamide hybridization solution is described in the Examples.

Because the anchor sequences are immobilized in a selected region on the support, the rate of hybridization of sample oligonucleotide sequence molecules to anchor sequence molecules is much slower than would occur if the two species were in solution. The rate can be increased by using the electric field to concentrate the sample molecules against the anchor surface. In this embodiment, the field is applied in the direction opposite to that used to extend the sample oligonucleotide sequence molecules after hybridized to the anchor sequence molecules. In particular, for concentration of the probes, the anchor sequence region is positive while for extension the anchor sequence region is negative. Such concentration increases the speed and thus the efficiency of hybridization by several orders of magnitude, and allow analysis of a small number of sample oligonucleotide sequence molecules. Typically, a field of 10 to 100 V/cm would be applied for 10 minutes to achieve concentration, then would be turned off for 1 min to allow free diffusion on the support. These cycles are preferably repeated for the duration of the hybridization.

After the sample molecules are hybridized to the anchor molecules, they are also highly concentrated against the surface. Thus hybridization of probe molecules to sample would also be accelerated by periodic application of the field as described above.

The anchor sequence/sample oligonucleotide sequence/probe complex is subjected to a separation means which moves unbound oligonucleotide sequences away from the anchor sequence. In a preferred embodiment, the separation means is an electric field which moves unbound probe and any unbound sample oligonucleotide sequences away from the anchor sequence in the direction of the field based on the charges inherent in oligonucleotide sequences.

The force of the electric field is sufficient to move unbound probe and any unbound sample oligonucleotide sequences in the direction of the field based on the charge on oligonucleotide sequences. However, the force is not sufficient to break long sample oligonucleotide sequences or to break the bonds in sample oligonucleotide sequence/anchor sequence complexes and thus remove sample oligonucleotide sequences which hybridized to the anchor sequence.

In general, the field should be about 1 to about 1000 V/cm, preferably 10 to 100 V/cm. A lower voltage is used when the sample oligonucleotide sequence is longer to avoid breaking the oligonucleotide sequence. In general the maximum voltage is inversely proportional to the length of the sample oligonucleotide. The time for extension of the sample oligonucleotide sequence is less than one minute. Time for removal of the unbound probes is 1 to 10 minutes. Therefore, the probes are preferably not detected until after 10 minutes in the electric field.

In any analysis where the position of the probes in relation to the anchor sequence is determined, the sample DNA must be extended. When the analysis is based on binding of a probe to the sample oligonucleotide sequence, as in determining whether two oligonucleotide sequences are on the same molecule of DNA or when presence of a disease gene sequence is detected, the sample oligonucleotide sequence need not be extended. However, even in such analyses, the sample oligonucleotide sequence is preferably extended to determine the distance of the probe from the anchor. This distance additionally provides information regarding the distance between two sequences of unknown location. Alternatively, when detecting a target oligonucleotide sequence of a disease gene, the distance can be used to confirm that the probe sequence is bound in the proper location in relation to the anchor sequence.

Extension of the sample oligonucleotide sequence can be performed using a magnetic bead at an end of the portion of the sample oligonucleotide sequence to be analyzed. Alternatively, the magnetic bead can be placed on the probes when the probes are sufficiently long to remain hybridized in the magnetic field.

Whatever the purpose of the assay, unbound probes must be removed. This can be done by extensive washing. Preferably, the probe can be attached to a magnetic bead or removed by use of an electric field which moves the charged probes in the direction of the field.

Alternatively, the separation means can be a magnetic field. In that embodiment, magnetic particles are bound to either the sample oligonucleotide sequence or, preferably, the probe prior to hybridization. Like the electric field, the magnetic field moves magnetic particle-labeled probe away from the anchor sequence in the direction of the field. In addition, probes which hybridize to the sample oligonucleotide sequence effectively provide a magnetic particle-labeled sample oligonucleotide sequence. If the probes are not attached to a magnetic particle, the probes can be removed by washing or by use of an electric field.

Thereafter, whether the probe is bound to the sample oligonucleotide sequence is determined by observing the presence of fluorescent-labeled probes on the support while the field is on. In addition, the positions of the bound probes, in relation to the anchor sequence can also be determined. The presence or location of the fluorescent probes can be determined with a fluorescent microscope, preferably an epifluorescent microscope, such as those commercially available for analysis of FISH assays. As is well known, the better the optics and the mechanical stability of the microscope, the higher the resolution which can be achieved.

The positions of the images of the probes in a field of view could be determined manually by comparison with a reticule in the eyepiece. When the sample oligonucleotide sequence is single-stranded DNA or RNA, the sample oligonucleotide sequence extends approximately 0.6 nm for each base (0.6 microns for each kilobase or 0.6 mm for each megabase).

A preferred detection technique for analysis of complicated probe patterns (e.g., as can be produced in some mapping embodiments or when the positions of several different probes are to be determined) is use of an electronic image detector (e.g., a TV camera), and a computer to analyze the image from the microscope and to control an X-Y stage holding the sample. Computer-implemented image analysis decreases the manual work required and can facilitate more accurate measurements of the positions of the probes.

To determine the position of a probe from the anchor as accurately as possible, a fluorescent bead attached to the probe should be no larger, and is preferably smaller than the wavelength of light emitted, which is typically 500 nm. If, for example, a bead 100 nm in diameter is used, the diameter of the image of the bead is larger by an amount approximately equal to the wavelength of light (i.e.; about 600 nm in diameter). The edge of the image of the bead appears diffuse due to the wave nature of light and distortions and imperfections in the optics of the microscope.

The position of the center of the disc-shaped image can be determined accurately by measuring the intensity of the image at many points, and thereby determining the center. One of many algorithms for determining the center would be to compute the center of intensity which is analogous to the center of mass. Many such algorithms are known and published.

To accurately determine the position of a bead, the diameter of the image of the bead should occupy at least about 1/100th of the linear field of view. Thus, if the image is detected using a conventional charge coupled device (CCD) camera, having about 1000×1000 pixels in a square array, the image is about 10 pixels across. The image then occupies about 80 pixels (a circle 10 pixels in diameter), and thus 80 values of its intensity are obtained. Such a field of view is 60 microns (100×600 nm), and thus encompasses about 100 kilobases. To characterize a longer sample oligonucleotide sequence, analysis of many overlapping fields of view, and reconstruction of the image of the entire specimen molecule can be performed. An accurate X-Y stage to move from one to another location to build up the image of the entire specimen molecule can be used. Such stages are commercially available.

The probes move during analysis due to thermal motion. The distance traveled by the probes, and thus the degree the image occupies a greater space than that of a stationary probe, depends on the time employed to capture the image. The time required varies depending on the brightness of the image and sensitivity of the camera system. If the system were to determine the probe position at an instant of time, that position would correspond to a particular configuration of the sample oligonucleotide sequence. However, it is the average configuration of the chain that provides the most useful information, since this average position can be correlated with nucleotide sequence of the sample oligonucleotide. This average position can be determined by obtaining an image which is blurred over time, since the intensities in that image represent the fraction of the total observation time that the probe was in a given position.

Various ways for performing the method depending on the type of analysis desired are described below.

Mapping

In mapping applications, the present method can determine whether a first oligonucleotide sequence and a second oligonucleotide sequence are on the same molecule of DNA, and the distance between those sequences which are on the same molecule. To determine whether a first and a second target oligonucleotide sequence are on a molecule of sample DNA, the sample DNA is contacted with an anchor sequence which hybridizes with the first target oligonucleotide sequence and with a probe which hybridizes with the second target oligonucleotide sequence.

As stated previously, when the sample DNA is not more than about 200 kilobases, no special handling techniques are required. However, since the mapping method is most informative with long DNA sequences, the sample DNA can be greater than about 200 kilobases and special handling is involved. Briefly, the sample DNA is prepared by lysing cells in a gel and adding a fragment of the gel to the support to which the anchor sequence is immobilized.

As in each embodiment of the method, the anchor sequence must be sufficiently long so that it only hybridizes to the first oligonucleotide sequence. Similarly, the probe must hybridize specifically to the second target oligonucleotide sequence. Generally, the probe is from about 10 to about 100 bases, preferably from about 20 to about 40 bases, most preferably about 30 bases.

After being subjected to the electric field, the sample oligonucleotide sequence is extended and the distance from the anchor sequence to the labeled probe is determined.

In a preferred embodiment of the method, hybridization of the sample DNA to the anchor sequence forms a double stranded oligonucleotide sequence having a site recognized by a restriction endonuclease and the restriction endonuclease is present in the hybridization buffer or added following hybridization. Following cleavage of the sample oligonucleotide sequence, only the portion of the sample oligonucleotide sequence which is remains bound to the anchor sequence is immobilized, allowing the determination of both the distance and direction of the probe from the anchor. Whether the 3' or 5' portion of the sequence remains hybridized to the anchor sequence depends on the placement of the restriction site within the anchor sequence. That is, when the restriction site is within a few nucleotides of one end of the anchor sequence, that end of the sample oligonucleotide sequence is does not remain immobilized. In a most preferred embodiment, there are two endonuclease sites, one on each side of the point the anchor nucleotide is attached to the solid support. In this case, either arm of the sample oligonucleotide sequence can be studied, depending on which endonuclease is used.

Prior art fluorescent in situ hybridization techniques are capable of determining the position of a unique sequence to within about 10 percent of the length of a chromosome; e.g., about 15 megabase pairs. Mapping the position to higher resolution usually requires construction clones of the DNA and looking for a clone that contains both sequences. If such a clone can be found, the two sequences are then known to be at least as close to each other as the length of the portion of the genome present in the clone.

This typically laborious process is accomplished in several stages, where at the length of the genomic insert in the cloning vector is progressively smaller in order to get higher resolution. If the two sequences are so far apart that even clones with the largest insert can not contain both, intermediate markers must be found, and the sequences related to them. Such progressive searching of a long region of the genome is sometimes called chromosome walking.

Direct visual mapping of the location using the method of this invention is clearly less labor intensive than chromosome walking. To determine the relative location of two oligonucleotide sequences, one of the two sequences must contain a target region which is sufficiently unique so that the region can be used to hybridize to the anchor sequences. The second oligonucleotide sequence must be sufficiently close to the first oligonucleotide sequence so that both oligonucleotide sequences are on the same molecule of DNA. Alternatively, a third, unique sequence that is close to (on the same DNA molecule as) the other two must exist.

This method becomes more powerful as the length of the specimen DNA increases, since sites in the genome that are more distant to each other are able to be related (mapped) to each other without the labor of using intermediate sequences. DNA molecules with lengths in excess of 1 megabases are routinely studied in laboratories using the special techniques discussed previously.

As longer sample DNA molecules are examined, the strength of the electric field may need to be decreased in proportion to the length in order to prevent the chain from being pulled apart.

There are situations in which one needs to know more sequence information, i.e., the nucleotide sequence of a longer stretch of the DNA, than is obtained by knowing that a short probe sequence has bound to a point on the DNA. One cannot just increase the length of the specific sequence of the probe. Since the sequence on the specimen DNA is not known, the likely result would just be that the probe would not bind anywhere, and one would only learn that the sequence was not present.

If the technique of polymerase chain reaction (PCR) is linked to direct visual mapping, and particularly if several species of distinguishable probes are used at one time, it is possible to determine a nucleotide sequence toward the end of a chain, use that sequence as a new anchor sequence and thus examine the region beyond it, and so on, i.e., walk the chromosome. The technique is illustrated in the Examples.

Identity Determinations

The method can be used to produce a characteristic pattern for a sample DNA sequence. Such patterns can be used to identify individuals. Preferably, the patterns are also produces in a test DNA sequence for forensic applications or to determine paternity.

The method comprises contacting the sample DNA with an anchor sequence comprising an immobilized, conserved oligonucleotide sequence and with a plurality of probes to form a hybridization mixture. Each of the probes comprises an oligonucleotide sequence of from about 5 to about 15 bases. Considerations for selection of the probe sequences were described previously. In this embodiment, all of the probes can have identical oligonucleotide sequences or a mixture of probes having different oligonucleotide sequences can be used. Following hybridization, the hybridization mixture is subjected to the field to move unbound oligonucleotide sequences away from the anchor sequence and extends the sample DNA in the direction of the field. The positions of the probes in relation to the anchor sequence are determined.

Preferably, when the analysis is to determine whether sample DNA and test DNA are from the same individual, the test DNA and the sample DNA are each contacted with the same anchor sequence and probes. Because this technique is based on the actual length of the oligonucleotide sequence between the anchor sequence and the probe (so long as the process of extending the sample oligonucleotide sequence is completed), the analyses of the sample and test DNA can be run at different times and even under different analysis conditions. The position of the fluorochrome-labeled probes is primarily determined by the structure of the sample molecule. This is in contrast to analysis methods such as polyacrylamide gel electrophoresis in which position is dependent on time of run, voltage, temperature, concentration of gel and so on. Preferably, however, the sample and test DNA are run simultaneously using the same assay conditions.

Following hybridization and separation of unbound oligonucleotide sequences, the positions of the probes from the anchor sequence are determined for the sample DNA and the test DNA. The positions are compared. When the probes are not in the same positions, the sample and test DNA are not from the same individual. When the positions match, the likelihood of a match can be determined statistically by well known methods.

The method can also be used to determine whether a putative father is the father of a child. For such analyses, sample DNA from the putative father, the child and the mother of the child are contacted with the same anchor sequence and probes. Following hybridization and separation of unbound oligonucleotide sequences, the positions of the probes from the anchor sequence are determined for the sample DNA and the test DNA. The positions of the probes on the child's DNA are compared to those of the mother. For any probes in the child's DNA which do not match to those of the mother, the positions of the unmatched probes are compared to the positions of the probes on the putative father's DNA. When those probes are not in the same positions, the putative father is not the father of the child. When the positions match, the likelihood that the putative father is the father of the child can be determined statistically by well known methods.

Detection of Sequences Characteristic of Alleles

In another embodiment, the method is used to determine whether a test oligonucleotide sequence is present in sample oligonucleotide sequence. The method comprises contacting the sample DNA with an anchor sequence and with a probe comprising an oligonucleotide sequence which binds to the test oligonucleotide sequence. The probe sequence can be any oligonucleotide sequence which binds to the test oligonucleotide sequence. In one embodiment, the test oligonucleotide sequence is sequence which is characteristic of a disease gene allele. For example, the test oligonucleotide sequence can be the F508 mutation which represents about 70 percent of the mutations of the gene for cystic fibrosis transmembrane conductance regulator (CFTR), the protein which is defective in cystic fibrosis (CF). However, any oligonucleotide sequence of interest can be detected. Other test oligonucleotide sequences can include, for example, sequences characteristic of the Y chromosome in fetal analyses or an HLA allele for tissue typing. In addition, the analysis can be used to detect mRNA for a particular gene, such as to determine the amount of expression of a gene of interest or to determine whether an oncogene is being expressed.

As discussed previously, a probe for such analyses recognizes a unique region, typically one which includes a unique sequence characteristic of a gene or one or more alleles of a gene. Because the probe is used to detect a unique region, the probe is from about 20 to about 30 bases, as discussed previously.

The method is based on binding of the probe. However, preferably, the distance of the probe from the anchor sequence is determined. This determination can be used to confirm that the binding is in the correct location and thus, is specific.

This method can be used with a plurality of different probes, each specific for a different test oligonucleotide sequence on the same DNA molecule. The distance from the anchor sequence of any probes which bind can be determined to determine which of the probes bound. Alternatively, each of the probes for a different test oligonucleotide sequence can be labeled with a different fluorochrome and the position of the probes can, preferably, be determined to confirm that the binding is in the correct location and is therefore specific.

This invention is further illustrated by the following specific but non-limiting examples. Procedures which are constructively reduced to practice are described in the present tense, and procedures which have been carried out in the laboratory are set forth in the past tense.

EXAMPLE 1

Preparation of Reagents and Device

Preferred reagents and a device of this invention are prepared as described below.

Oligonucleotide sequences

The oligonucleotide sequences for the anchor and probe are purchased from The Midland Certified Chemical Company, Midland, Tex. which prepares custom oligonucleotide sequences using phosphoamidite chemistry and purifies them by anion-exchange HPLC. The modified nucleotide containing the amino group can be at either end on at any internal position. They also supply oligonucleotides with an amino group on a 6-carbon spacer, which in some cases allows for more efficient binding of the complementary oligonucleotide sequence.

Assembly of device

Method A. A gold surface (approximately 180 nm thick) on the support is prepared by evaporation on a chromium-coated (approximately 4 nm thick) edge of a 10×10×1 mm thick silicon slab. The gold surface is then coated by an aminotrithiol, preferably tris(3-thiolpropyl) glycylaminomethane ($HSCH_2CH_2CH_2)_3CNHCOCH_2NH_2$, as described in Whitsell and Chang, *Science* 261:73 (1993). Briefly, the gold surface is coated by immersion in a 1 mM deoxygenated ethanolic solution of the aminotrithiol for 6 hours, as described by Laibinis and Whitesides, *J. Am. Chem. Soc.* 114:1990, (1992). The surface is then washed 3 times with distilled water. In this procedure the thiol groups are bound to the gold while the amino groups remain free on the surface and thus can be linked to other molecules.

Anchor sequence oligonucleotides are coupled to the amino groups on the gold surface by reaction with a primary amino group present on an internal modified nucleotide. The coupling between the two amino groups is accomplished by reaction with glutaraldehyde as described by Alpin and Hughes, *Anal. Biochem.* 113:144 (1981). Briefly, the surface is covered with a 0.25 percent solution of glutaraldehyde in PBS (phosphate buffered saline, 0.15M NaCl, 0.01M sodium phosphate at pH 7.0) and held at room temperature for 30 minutes. The surface is then washed 3 times in excess PBS.

Two silicon rectangles are attached using epoxy cement to a glass microscope slide which serves as the support with the two gold coated edges parallel and facing each other and about 10 mm apart. One gold surface has been coated with anchor oligonucleotides, the other serves only as an electrode. Two, 4 cm long, 28 gage, nichrome wires are then attached using epoxy cement to the microscope slide, each with one end contacting a gold surface of one electrode, and then leading off the slide to provide electrical connection through longer standard leads to the power supply.

A glass coverslip is placed on top of the two silicon rectangles, creating a 1×10×10 mm detection chamber, which thus has a volume of 100 µL. Fluid is introduced at the edge of the chamber and is drawn in by capillary action. Alternatively, the coverslip is removed, a drop containing 100 µl of fluid is applied between the two silicon rectangles, and the coverslip is replaced.

Fluid may be removed, for example in washing procedures, by applying a piece of filter paper at one edge of the chamber and drawing the fluid into the paper. Alternatively, the cover slip may be removed and the entire slide immersed in a small container containing washing solution. This later procedure is used when the temperature must be precisely controlled.

Method B. A gold surface (approximately 180 nm thick) on the support is prepared by evaporation on a chromium-coated (approximately 4 nm thick) edge of a 10×10×1 mm thick glass slab. The gold surface is then removed over a 0.005×3 mm rectangle by scratching the gold surface with a sharp needle. Amino groups on anchor sequence oligonucleotides are attached to an amino-derivatized glass surface on the support as described by Alpin and Hughes in *Anal. Biochem.* 113:144 (1981). Briefly, the exposed glass surface is first derivatized by treatment with 3-amino propyl trimethoxy silane (Sigma Chemical Co., St. Louis, Mo.) for 4 minutes at room temperature. The resulting amino groups on the glass surface of the support and the amino groups on the anchor sequence oligonucleotide are then cross linked with glutaraldehyde.

Preparation of probes

Polystyrene spheres, approximately 200 nm in diameter and containing fluorescent dyes (G230 green, R200 red) are purchased from Duke Scientific Corporation, Palo Alto, Calif. A pendant chloromethyl group is introduced by reaction with HCl and formaldehyde, then coupled to Boc-alaninel$_{12}$ in the presence of triethylamine, and the protecting group is removed from the terminal alanine with trifluroacetic acid in dichloromethane (the standard chemistry used in solid phase peptide synthesis). The resulting amino group is linked to a 5' amino group on the probe oligonucleotide using glutaraldehyde. The reaction conditions at the addition of Boc-alaninel$_{12}$ are adjusted so that between 10 to 100, preferably 20, peptides are added. Thus the beads are finally negatively charged, due to the oligonucleotides, with the value of the charge being about 20 times the number of nucleotides in the probe.

Preparation of sample DNA from Blood

DNA is extracted from blood using a QIAGEN blood DNA kit (Qiagen Inc., Chatsworth, Calif.) according to the manufacturer's directions. One ml of whole human blood yields approximately 20 micrograms of DNA using the Qiagen TIP 20 purification device. After purification, DNA is denatured by incubation at 100° C. for 3 minutes, and is diluted immediately into hybridization buffer to obtain a final concentration of not greater than 1 µg/ml to minimize self-hybridization between molecules of sample genomic DNA with approximately complementary sequences.

Hybridization

The preferred hybridization procedure is described by Wood et al. in *Proc. Natl. Acad. Sci. (US)* 82:1585 (1985). The use of tetramethylammonium chloride in the final hybridization buffer results in equal stability for AT and GC base pairs, and thus the dissociation temperature of an oligonucleotide hybrid is dependent only on the length of the complementary sequence and not on its base composition.

Briefly, the Wood et al. hybridization procedure consists of five steps (a through e) described below:

a. Prehybridization: The chamber and attached anchor sequences are incubated with a solution that coats surfaces which could bind oligonucleotides non-specifically to prevent non-specific binding in the subsequent stages. The chamber is treated for 4 hours at 37° C. with a solution of 6× SSC and 5× Denhardt's containing boiled sonicated salmon sperm DNA at 0.1 mg/ml. SSC is 0.15M NaCL, 0.015M trisodium citrate, pH 6.8. 100× Denhardt's solution is 2% Ficoll (M.W. 400,000), 2% polyvinyl pyrrolidone (M.W. 400,000), and 2% bovine serum albumin and is stored at 20° C.

b. low-stringency hybridization of sample DNA to anchor sequences: Denatured sample DNA, in the prehybridization solution (6× SSC and 5× Denhardt's containing salmon sperm DNA), and additionally containing dextran sulfate at a concentration of 100 mg/ml, is allowed to hybridize to the anchor sequence for 16 hours at 37° C.

c. high-stringency washing to remove non-specifically bound sample DNA: The chamber is washed three times with SSC at 4° C. and twice for 30 minutes with 6× SSC at 4° C. The chamber is then washed three times with Me₄NCl wash solution at 37° C. Me₄NCl wash solution is 3.0M Me₄NCl, 0.05M Tris-HCl pH 8.0, 0.002M EDTA and sodium dodecyl sulfate at 1 mg/ml. The chamber is finally washed twice for 30 minutes in the Me₄NCl wash solution at 4° C. below the dissociation temperature, Td, corresponding to the length of the anchor oligonucleotide. The Td values for oligonucleotides of various lengths are given by Wood et al. in *Proc. Natl. Acad. Sci. (US)* 82:1585 (1985), and are approximately:

| PROBE LENGTH | Td (°C.) |
|---|---|
| 11 | 45 |
| 13 | 47 |
| 15 | 49 |
| 20 | 59 |
| 30 | 69 |

The Td for other lengths are estimated by interpellation or extrapolation.

If one arm of the sample DNA is to be removed through use of a restriction endonuclease, the chamber is washed with a buffer compatible with the enzyme, and the enzyme is added. After an appropriate time of incubation the chamber is washed with two times with the hybridization buffer used in stage b.

d. low-stringency hybridization of oligonucleotide probes to sample DNA: The hybridization solution containing probes is added to the chamber and hybridization is carried out as in step b, except that the temperature is reduced to 20° C. when the probe sequence is less than 15 nucleotides long.

e. high-stringency washing to remove non-specifically bound probe oligonucleotides: The procedure is carried out as in step c, except that the temperature is appropriate to the length of the probe oligonucleotide as described above.

Analysis procedure

After all steps of the hybridization are carried out, the chamber is washed three times with SSC, filled with SSC and placed on the stage of an epifluorescence microscope. A 10 volt potential is applied across the two gold electrodes, with the anchor sequence-containing electrode being negative. After 2 minutes, fluorescent beads are located at low magnification (field of view 1 mm) by inspection. The magnification is increased so that the field of view is 200 microns, and a photograph is taken. The magnification is increased so that the field of view is 20 microns, and 10 successive photographs are taken starting at the anchor surface and progressing to the positive electrode, in order to obtain a panorama of the probe beads hybridized to the extended sample DNA chains.

EXAMPLE 2

Mapping Alleles of the Cystic Fibrosis Transport Regulator (CFTR) Protein Gene

The sequence of the mRNA coding for the CFTR protein has been reported by Riordan et al., *Science*, 245:1066 (1989), and considerable information has been obtained regarding the gene itself. The mRNA is 6.2 kb long and codes for a protein of 1480 amino acids. The gene is 230 kb in length, and contains 27 exons.

Segments of the genomic sequence totaling 22.7 kb have also been obtained by Zielenski et al., *Genomics*, 10:214 (1991). The emphasis in the Zielenski study was on the boundaries of the exons since mutations in those regions frequently result in aberrant splicing and non-functional protein. A 640 nucleotide segment of the genome about 4.4 kb upstream of the start of the CFTR gene has been reported by Jones and Winistorfer, *Nucleic Acid Res.* 20:595 (1992), Genebank number L06116. That portion of the genome is used to hybridize to an anchor sequence for further analysis of the gene in this study.

The nucleotide sequence reported by Jones and Winistorfer contains an EcoRI site towards the end proximal to the CFTR gene. The last 31 nucleotide portion of that sequence is illustrated below, with the EcoRI site underlined (a space is inserted every tenth nucleotide for reference):

5' tgaattcaaa ggaaaacata agatgcaatt c 3' (sequence ID 1)
3' acttaagttt cctttttgtat tctacgttaa g 5' (sequence ID 2)

Sequence 2 is prepared with an amino linker on the cytosine at position 12 as described in Example 1, and is used as an anchor sequence to obtain fragments of genomic DNA containing the CFTR gene. The anchor sequence is attached to the support by Method B as described in Example 1. Hybridization is performed as described in Example 1, using 66° C. as the temperature for the final wash following hybridization with the following exception. Following hybridization, 5 units of EcoRI (Sigma Chemical Co.) in 100 µl of buffer (100 mM Tris HCl pH 7.5, 10 mM MgCl₂, 50 mM NaCl, 100 µg/ml BSA) is added to the chamber and incubated at 37° C. for 60 minutes. The wash step is then repeated. After the incubation with EcoRI (the enzyme cuts between g and a on both strands at the underlined site), the portion of the sample DNA upstream of the CFTR (that is not wanted), is bound to the anchor by only two base pairs, and is thus eliminated by the subsequent washing steps.

A 12 nucleotide probe specific to the three nucleotide deletion mutation delta F508, (aac acc gat gat (sequence ID 13) is made (the delta F508 sequence given in Riordan et al., *Science*, 245:1066 (*1989*)). The first half of this probe can hybridize to sample DNA not containing the delta F508 mutation at either the 6 nucleotides coding for the isoleucine-isoleucine sequence 5' to the 508 deletion, or to the 6 nucleotide sequence coding for glycine-valine 3' to the 508 deletion. However, all 12 nucleotides can hybridize to sample DNA having the delta F508 mutation. The probe is labeled with red fluorescent beads.

A 12 nucleotide probe specific to the one nucleotide deletion mutant CF3821delT (White et al., *Genomics* 10:266 (1991)), gaa gga atg ttc, (sequence ID 3)

is made and labeled with green fluorescent beads as described in Example 1. This probe can only hybridize to 7 nucleotides of sample DNA that do not contain this mutation.

The probe is used to screen the sample DNA for these specific CFTR mutations from a blood sample to be tested for the mutations. DNA is obtained from a blood sample as described in Example 1. The test procedure is performed as described above. Following analysis by determining the presence of the appropriate colored fluorochromes, the sample is shown to contain DNA that has the delta F508 mutation.

EXAMPLE 3

Mapping

The following example illustrates determining the nucleotide sequence of a segment of a long sample DNA by walking the chromosome.

The sample oligonucleotide sequence is human genomic DNA prepared from a blood sample as described in Example 1. An anchor sequence having sequence no. 1 is prepared as described in Example 2. The sample DNA is hybridized to the anchor sequence as described in Example 2, and then incubated with EcoRI restriction endonuclease to remove one arm of the sample DNA molecule. The remaining arm is hybridized to the following seven probes. The sequences for the probes is obtained from a table of random numbers. The number following each sequence is the sequence identification number (sequence IDs 4–10).

| probe sequence | fluorescent dye | identifier |
|---|---|---|
| ttgaatt (4) | red | 1 |
| gttgcaa (5) | green | 2 |
| cggctcg (6) | blue | 3 |
| cggactg (7) | red and green | 4 |
| gatagga (8) | red and blue | 5 |
| atgggag (9) | green and blue | 6 |
| aggaacg (10) | red, green and blue | 7 |

Each species of probe oligonucleotide is attached to a bead containing one of three fluorescent dyes, or a combination of dyes, so that each of the seven probes is distinguishable by examination in the fluorescent microscope using different excitation wavelengths (an arbitrary identifier number from 1 to 7 is used to refer to the seven species of probes in the above table). The images obtained are digitized and analyzed by computer in order to identify the dye combination as described by Ried et al., *Proc. Natl. Acad. Sci. USA* 89:1388 (1992).

At low magnification a field of view is selected that contains at least 4 sample molecules (which are seen only by the fluorescent probes that have hybridized to them). The magnification is increased to obtain a field of view of 20×20µ, and eight overlapping images are obtained starting at the anchor surface and extending to 120µ past the anchor toward the opposite electrode. The X-Y positions of the probes are determined by the image analysis portion of the computer program. Since the hybridization efficiency is not 100 percent, not all sites on all molecules are occupied by probes. However since the image is a composite of at least 4 sample molecules, all the hybridization sites can be identified.

Most of the segments between the probes can be selectively amplified using the polymerase chain reaction (PCR) using the following method. Each probe species hybridizes to a site on the sample DNA occurring on average every 16,000 nucleotides, or an average of 12.5 sites on the 200,000 nucleotides that are examined. The total sites for all seven probe species is 88 sites, and the average distance between sites is 2,300 nucleotides. There are 49 species of DNA segments between probes, one for each of the possible combinations of the 7 probes. Each of these 49 segment species can be selectively amplified using the sample DNA as the template, the anchor distal probe as one primer, and the complement of the anchor proximal probe as the other primer. On average there are about two of each of the 49 species of segments on any sample DNA sequence of about 200,000 nucleotides, and in the majority of cases these two segments have sufficiently different lengths that they can be separated by PAGE. The nucleotide sequence can then be determined by any of the standard methods.

Selective amplification of a segment toward the distal end of the sample DNA allows preparation of a new anchor oligonucleotide which allows examination of another 200,000 nucleotide sequence of the genomic DNA distal to the first sample DNA. Using the image of the sample DNA, a segment is chosen that is less than 2,000 nucleotides long, is distinct in length from the other segments of that species, and is toward the anchor distal portion of the sample DNA. This procedure is implemented in the following section.

Two probe 3–6 segments are observed on the sample DNA (probe 3 being closest to the anchor), one segment close to the distal end of the sample was 1,500 nucleotides long, and the other was closer to the anchor and was 3,000 nucleotides long. The sample DNA is removed from the anchor by heating the chamber at 70° C. for 3 minutes, and the 3–6 segments were amplified by PCR in the standard manner. The desired 1.5 kb product is isolated using polyacrylamide gel electrophoresis (PAGE) with an acrylamide concentration of 3.5 percent. The nucleotide sequence of the 1.5 kb product is determined. The 1.5 kb product also contains an EcoRI restriction site. An anchor sequence containing the site at the 5' end of the anchor is prepared and the procedure is repeated. This cycle can in principle be repeated until the telomere is reached. Such characterization of a long stretch of DNA by successive steps has been called chromosome walking (see for example pg 131 of *Biochemistry*, L. Stryer, 3rd ed., W. H. Freeman and Company, New York, 1988).

EXAMPLE 4

Preparation of Reagents and Device

Construction and use of electrophoresis chamber

A DNA analysis device of this invention was prepared as described below. A DNA detection chamber (or electrophoresis chamber) constructed from a square frame of polyacrylamide gel (gel frame) sandwiched between two glass microscope coverslips. The bottom of the device was a generally planar support comprising a 50×75 mm coverslip (large coverslip) which provided support for two wire electrodes and buffer connecting the electrodes to the edge of the gel frame. A cavity formed in the gel as described below was sealed by a cover which was a 20×20 mm coverslip.

To prepare the electrophoresis chamber, a large cover slip, 50×75 mm, was immersed in acid dichromate cleaning solution overnight. After thorough washing in water and drying, one surface was treated with 10M NaOH for 10 minutes at room temperature and again washed with water and dried. This surface was then treated with 3-meth acryloxy propyl trimethoxy silane (Polysciences, Inc., Warrington, Pa.) for 10 minutes at room temperature and again washed with water and dried.

A 1 mm thick slab of polyacrylamide gel was formed on top of this coverslip by constructing a chamber closed at two ends with pieces of a glass microscope slide 1 mm thick, and another piece of a glass slide on top. A solution containing 20 percent acrylamide, 1 percent bis-acrylamide, 1 percent by volume of a 10 percent sodium persulfate solution, and 0.1 percent by volume of TEMED (N, N, N', N',-tetramethylethylenediamine), (Sigma Chemical Co., St. Louis, Mo.), was introduced into the chamber. (All solutions are given in weight percent (gm per 100 ml) unless otherwise specified.) Exposure of the glass surface to 3-meth acryloxy propyl trimethoxy silane covalently linked this monomer to the glass surface, and during subsequent polymerization of the gel slab this acrylamide monomer was co-polymerized into the polyacrylamide gel, thus linking it to the glass. A tight bond between the bottom of the gel and the glass surface was important to the overall method, since it prevented electro-osmotic flow under the gel.

Approximately 60 minutes was allowed for polymerization, and the side and top glass pieces were removed and the gel slab was trimmed with a razor blade to a 10×10 mm square. A 5×5 mm square was cut and removed from the middle of the gel, forming a cavity which functioned as the electrophoresis chamber. An electrophoresis solution containing the hybrid structures to be observed (preparation of the hybrid structures is described below) was introduced into the chamber and a small (20×20 mm) cover slip was placed on top, sealing the chamber.

A support for the DNA analysis device was constructed from a 60×100 mm piece of 3 mm thick transparent LUCITE sheet with a 30×30 mm square hole cut in the middle. Since the sheet functioned only to support the device and to anchor the electrodes, the support can be of any material. The sheet material can be transparent or opaque and is preferably dielectric. However, since the support which forms the electrophoresis chamber is an insulator, the sheet material can be conductive. The hole was cut in the center to permit use of an inverted epifluorescent microscope (which has an objective on the bottom of the microscope). A hole in the support is not needed for a conventional microscope. Two 22 gauge nichrome wire electrodes, approximately 50 mm long were attached to one of the long sides of the Lucite by two brass bolts approximately 50 mm apart. (22 gauge wire has a 0.32 mm diameter.) The wires extended, parallel to each other, over the surface of the LUCITE sheet toward the opposite edge. The chamber assembly was placed on the sheet and slipped under the wire electrodes, with the electrophoresis chamber between the electrodes and over the square hole in the sheet.

Several milliliters of buffer was applied to the surface of the large coverslip between each electrode and the nearby chamber edge to create a pool of liquid connecting the electrode and the gel edge. The two brass bolts were connected by flexible wires to a DPTT (double pole, triple throw) switch by the side of the microscope, and the switch was connected to an electrophoresis power supply. The power supply was turned on before observation, and the voltage adjusted to the desired value, typically between 20 and 50 volts. The DPTT switch was connected so that the observer could apply the voltage in either polarity or turn it off, while looking through the microscope. Typically 50 volts was used, which resulted in a current of 5 ma passing through the chamber.

During prolonged observation, significant water evaporated from the pools of buffer and several drops of distilled water were added to restore the volume. Gas evolved from the electrodes, but did not disturb the chamber as long as there was about 10 mm between the electrodes and the chamber. Observation times of up to 30 minutes were performed. Chemical decomposition of the nichrome wires was observed and platinum wires, although more expensive, are preferred for long term use.

A Ziess inverted fluorescent microscope was used to observe the hybrid structures. The square hole in the Lucite allowed the objective to closely approach the bottom of the chamber. Typically a 40× objective was used, which had a working distance of about 0.35 mm. Since the bottom coverslip was 0.20 mm thick, the bottom 0.15 mm (150 microns) of the chamber could be observed.

Photographs were taken with an Olympus 35 mm camera. An intermediate lens with a magnification of 3.2, in combination with the 40× objective, produced a total magnification on the film of 128×. One standard frame on 35 mm film is 24×36 mm, which thus represented a visual field of 188×281 microns in the electrophoresis chamber. The depth of field with this objective was about 2 microns.

Kodak color print film with a speed of ASA 1000 was used, and an exposure of 1/16 th of a second was found to produce optimal results using the standard Ziess high pressure Hg arc lamp. The images on the film were transferred to a Kodak Photo CD and were read and analyzed using an Macintosh IIfx computer (Apple Computer, Inc., Cupertino, Calif.) and the Photoshop software package (Adobe Systems, Inc., Mountain View, Calif.).

Preparation of fluorescent probes

Polystyrene beads 0.5 microns in diameter, containing internal green fluorescent dye and surface carboxyl groups were purchased from Duke Scientific Corp., Palo Alto, Calif. One ml of the 1 percent solid suspension supplied by the manufacturer was mixed with 300 µl of a solution containing 5 mg/ml EDC (1-ethyl-3-(3-dimethylaminopropyl)-carbodimide hydrochloride) and 1 mg/ml of sulfo-NHS (sulfo-N-hydroxy-succinimide, both purchased from Pierce Chemical Co., Rockford, Ill.) in 0.1M MOPS (4-morpholine propane sulfonic acid, Sigma Chemical Co., St. Louis, Mo.) at pH 7.5. To this mixture was added 60 µl 1M NaCl, 15 µl carrier DNA (degraded free acid from herring sperm, Cat. D3159, Sigma Chemical Co., St. Louis, Mo., at 100 mg/ml brought to pH 7 with NaOH), and 120 µl water. Finally, 5 µl of the oligonucleotide probe (0.45 mM in water) containing a 5' terminal primary amine group on a 12 carbon spacer (National Biosciences, Inc., Plymouth, Minn.) was added. In this example the probe nucleotide sequence was:

cgc gcc ctc gta tca c (sequence ID 11)

The probe sequence is complementary to nucleotides 47,469 to 47,484 on the L strand of bacteriophage Lambda.

The suspension was agitated at 45° C. for 2 hours on a shaker at 150 rpm. To block any unreacted groups on the beads, 15 µl of ethanol amine was added and incubation continued for an additional hour. The bead suspension was then centrifuged for 10 minutes in an Eppendorf microcentrifuge at 10,000 rpm. The supernatant was discarded and the bead pellet was resuspended in 1.5 ml of water. Centrifugation and resuspension was repeated for an additional 4 times to ensure complete removal of any unreacted probe oligonucleotide that could complete with the bead linked oligonucleotide. The final pellet was resuspended in 1.0 ml of water.

The extent of oligonucleotide-bead linkage was measured in order to optimize the conditions used in the linkage, and as quality control for the method. The 3' end of the probe oligonucleotide had a free OH group and thus served as a substrate for terminal deoxynucleotidyl transferase. This enzyme was purchased from United States Biochemical Corp., (Cleveland, Ohio). Buffer and directions for end labeling were supplied by the manufacturer, and were used to incorporate alpha $^{35}$S labeled dideoxyadenosine triphosphate (ICN Biomedicals, Inc., Irvine, Calif.).

Size exclusion chromatography using P6 (Bio-Rad) was used to separate the labeled oligonucleotide, which eluted at the void volume, from unincorporated triphosphate. In one typical linkage reaction, 13 percent of the total probe oligonucleotide was linked to beads, which corresponded to 45 oligonucleotides per bead. While only one oligonucleotide is required to hybridize a probe bead to a sample DNA molecule, a larger number increases the probability that a bead will hybridize after a random collision, and thus improves the kinetic rate of the hybridization.

Preparation of anchors and hybrid structure

Method A

Preparation of anchors: Activated agarose balls, were purchased (Affi-gel-15, Bio-Rad Laboratories, Hercules, Calif.) and served as a solid phase for attachment of an anchor oligonucleotide sequence. Although the agarose balls were conveniently used, any solid phase, including the support for the electrophoresis chamber, can function as the solid phase. The agarose balls were 75–300 microns in diameter and contained N-hydroxy-succinimide groups on a 15 atom spacer attached to the agarose. The spacer contained a positively-charged amino group which made it preferable for coupling to the negatively charged anchor oligonucleotide.

To 2 ml of the 1:1 gel suspension supplied by the manufacturer, 10 ml of cold water was added and the suspension was centrifuged at 1500 rpm in a SORVALL RT6000B centrifuge and swinging bucket rotor at 4° C. for 2 minutes. The supernatant was discarded and the pellet was washed two more times in 10 ml of cold water. To 0.8 ml of the gel and 0.1 ml of water remaining from the wash, 0.2 ml of 0.5M MOPS, pH 7.5, 10 gl carrier DNA, and 40 µl of a 0.5 mM solution of the anchor oligonucleotide sequence containing a primary amine at the 3' terminus (National Biosciences, Inc., Plymouth, Minn.) in water were added. In this example the anchor oligonucleotide sequence was:

cgc gag gtc gcc gcc c (Sequence ID 12)

which sequence is complementary to nucleotides 1–16 of the L strand of bacteriophage Lambda.

The suspension was mixed gently for 2 hours at 25° C. In order to block all activated groups that had not reacted with the anchor oligonucleotide sequence, 10 µl of ethanol amine was added and incubation continued for an additional 1 hour. The suspension was then washed 5 times in 20 ml of SSC in order to remove any traces of unreacted oligonucleotide that might compete with the bound oligonucleotide for a sample DNA sequence. The suspension was stored at 4° C. as a 1:1 slurry in SSC (standard sodium citrate, 0.15M NaCl and 0.015M sodium citrate at pH 7.0) and 0.04% sodium azide.

Since the anchor oligonucleotide sequence did not have a free 3' OH group, the sequence cannot be labeled using terminal deoxynucleotidyl transferase as was done to measure the extent of linkage of probe oligonucleotides to beads. Thus, an oligonucleotide complementary to the anchor oligonucleotide, and with a free 3' OH group, was purchased and labeled as described for the probe oligonucleotide. This labeled complementary oligonucleotide was then used to measure the capacity of agarose anchors to hybridize the complementary oligonucleotide.

Aliquots of agarose anchors were hybridized in mixtures containing the same amount of radioactive complementary oligonucleotide and increasing amounts of non-radioactive complementary oligonucleotide. The total amount of complementary nucleotide that results in half maximal isotope hybridization is a measure of anchor capacity. Ten µl of packed agarose from one typical preparation required 700 pico moles of oligonucleotide to depress hybridization 50 percent.

Preparation of hybrid structures: One µl of 20× SSC was added to 20 µl of anchor agarose slurry, the suspension centrifuged briefly and 11 µl of the supernatant discarded. To the remaining suspension were added 3 µl of carrier mix, consisting of 10 parts of a 10% SDS (sodium dodecyl sulfate) solution to 1 part carrier DNA, 10 µl of a freshly sonicated probe bead suspension, 3 µl of formamide, and 2 µl of denatured sample DNA at a concentration of 10 µg/ml. Sample DNA (United States Biochemical Corp., Cleveland Ohio) had been purified from bacteriophage Lambda and was denatured by heating to 100° C. for 3 minutes. The resulting suspension was gently mixed and incubated at 37° C. for 20 hours in capped polyethylene tubes in order to allow hybridization to occur. The tubes, with an internal volume of about 70 µl, were made by cutting the bottom 10 mm from 50 mm long, 0.4 ml centrifuge tubes.

Purification of hybrid structures: The great majority of the probe beads were not expected to be hybridized to the sample DNA. Sample DNA hybridized to an anchor sequence and to probe DNA which was bound to the agarose balls was purified from excess beads to remove non-hybridized probe DNA. The hybrid structures were expected to be sensitive to hydrodynamic shear, and thus the purification was designed to reduce shear to a minimum.

The body of a 10 ml disposable syringe was fitted with a Lour lock stopcock (Bio-Rad Laboratories) and a 0.4 ml polyethylene centrifuge tube was press fitted on the end of the stopcock. Two ml aliquots of five solutions of decreasing concentrations of sucrose (25, 20, 15, 10, and 5 percent) in ⅕× SSC were introduced into the syringe, which was held by a clamp in a vertical position with the centrifuge tube on the bottom. A 1 mm diameter capillary tube was inserted into the syringe from the top, through the open stopcock into the bottom of the centrifuge tube, and the 25 percent sucrose solution introduced. The air was thus displaced as the solution was added and bubbles could be removed by rapid pulsation of the fluid. The remaining 4 solutions, in order of decreasing concentration, were gently layered at the top of the fluid in the syringe.

A section of the end of a 28 gauge hypodermic needle was bend at 45 degrees and this section forced through the excess plastic at the tip of the tube containing the hybrid structures. The tube cap was removed and by holding the needle, the tube, open end first, was immersed in the sucrose solution at the top of the syringe which was inclined at a 45 degree angle. The needle was held in place with a small cardboard square having a notch cut at one edge, and the syringe was slowly returned to its original vertical position. The agarose balls fell out of the tube and down the sucrose gradient through the stopcock and into the centrifuge tube. This process required about 60 minutes.

The polystyrene beads have a lower density than the bottom layer of sucrose, and also sediment at less than 1/10,000 the speed of the agarose balls. Thus, beads that were not attached to agarose balls remained at the top of the gradient. After the agarose balls had settled to the bottom of the tube, the stopcock was shut and the tube removed from the syringe.

Observation of hybrid structures: Using the electrophoresis chamber, numerous hybrid structures with the characteristics expected for a sample DNA molecule hybridized at one end to the anchor sequence and the other end to the probe sequence were observed. The defining property was the extension of the bead to a fixed length when the electric field was applied, followed by a slow relaxation of the bead to its original position when the field was turned off. In addition, structures were seen with many beads tangled together which also extended and relaxed in the electric field. However, these tangled structures were easily distinguished from the ones representing single DNA molecules.

One structure was chosen for quantitative measurement. Six pairs of photographs were taken, the first member of each with the electric field off and the second after the field had been turned on for approximately 15 seconds. The moveable end of this structure was associated with two beads that were apparently tangled with each other, separated by 2 to 4 microns. The average movement of the two beads after the field was applied is illustrated below:

| Film frame | Movement (microns) |
| --- | --- |
| 9 to 10 | 33.9 |
| 11 to 12 | 37.3 |

The linear extension of single stranded DNA and, in particular, the linear extension per nucleotide in an electric field, has not been reported in the literature. (Only double stranded DNA, which is more compact, has been observed. However, one can estimate an extension of 0.6 to 0.7 nm per nucleotide. Thus, one would expect an extension of 0.6×47,484 to 0.7×47,484 or 28.5 to 33.2 microns. The observed extensions were compatible with the values observed in this study within the uncertainties of measurement and DNA structure.

Method B

Preparation of anchors: A 100:3:1 mixture of acrylamide, bis-acrylamide (Sigma Chemical Co., St. Louis, Mo.), and 2-acrylamide glycolic acid (Aldrich Chemical Co. Inc., Milwaukee, Wis.), at a total concentration of 200 mg/ml, was prepared in NME buffer (0.1M NaCl, 0.01M MOPS pH 7.5, 0.001M EDTA) and polymerized as in Method A to form 1×2×4 mm gel bars. Anchor oligonucleotides containing a 3' terminal primary amino group were linked to the carboxyl groups on the bars of the acrylamide copolymer using EDC and sulfo-NHS as described for the preparation of oligonucleotide fluorescent probes. The bars were washed for 4 hours with 1 ml of NME buffer per bar to remove unlinked oligonucleotide. This wash was repeated 3 times and the bars were stored at 4° C. in NME buffer.

Preparation and observation of hybrid structures: One anchor bar was immersed in 100 µl of denatured sample DNA (40 µg/ml in NME buffer, heated to 100° C. for 3 minutes) and incubated at 37° C. for one hour to allow hybridization. The bar was then washed gently 4× with 1.5 ml aliquots of NME buffer to remove unhybridized DNA, in particular, the strand of DNA not complementary to the anchor sequence which can hybridize to and then displace a strand of DNA hybridized to the anchor. The anchor bar was then placed into the electrophoresis chamber, and the chamber was filled with a 1 to 10 dilution of oligonucleotide fluorescent probe in NME buffer.

Using the microscope, a flat portion at the edge of the anchor bar was located, and an electric potential of 20 V (− to + toward the surface) was applied for 30 seconds. Fluorescent probe beads in a zone extending approximately 300 microns out from the anchor bar were transported to the surface of the anchor during this time. The electric field was turned off, and the layer of beads that had accumulated diffused away from the surface. At 20 seconds the layer of beads was about 10 microns thick, and the field was turned on for 1 second, which again compressed the layer of beads against the anchor surface.

The off for 20, on for 1 second, cycle was repeated for a total time of 5 minutes. The electric potential was then reversed and the great majority of beads moved away from the anchor surface. After 10 seconds, a zone at the edge of the anchor surface had been cleared sufficiently of beads so that it was possible to see single beads. Clusters of beads were seen that extended out from the anchor surface by more than 10 microns, and which beads fell back on the surface when the field was turned off. These structures were consistent with probe beads tangled in sample DNA molecules.

In this method the electric field was first used to concentrate probe beads approximately 30-fold to facilitate hybridization to sample DNA at the anchor surface. The electric field was then used to remove unhybridized probe beads from the vicinity of the anchor surface to facilitate observation of hybrid structures. The probe beads move toward the + electrode in an electric field primarily because of the negative charge of about 100,000 from the persulfate groups used to initiate polymerization of the styrene. The electric field can also be used to concentrate sample DNA at the anchor surface, since the sample DNA molecule has a negative charge of about 50,000 but a hydrodynamic diameter of about 0.1 micron, 1/5th the diameter of the beads.

What is claimed is:

1. A method for analyzing a sample oligonucleotide sequence comprising:
   (a) contacting a said sample oligonucleotide sequence with an anchor sequence comprising an oligonucleotide sequence which is immobilized to a support and which hybridizes with said sample oligonucleotide sequence and with a probe comprising an oligonucleotide sequence which hybridizes to a target oligonucleotide sequence to be detected in a suitable buffer to form a complex;
   (b) subjecting said complex to a field which moves unbound oligonucleotide sequences away from said anchor sequence in the direction of said field, wherein said field is a magnetic field and a magnetic particle is attached to said sample oligonucleotide sequence or said probe or said field is an electric field; and
   (c) determining whether said probe is bound to said sample oligonucleotide sequence.

2. The method of claim 1 wherein said probe is labeled with a fluorochrome and determining whether said probe is bound to said sample oligonucleotide sequence is performed by observing the fluorochrome with a fluorescent microscope.

3. The method of claim 2 wherein said fluorochrome is present in a bead.

4. The method of claim 3 wherein said bead is plastic.

5. The method of claim 4 wherein said plastic bead is a polystyrene bead.

6. The method of claim 1 wherein said anchor sequence is from about 10 to about 100 bases.

7. The method of claim 4 wherein said anchor sequence is from about 20 to about 40 bases.

8. The method of claim 1 wherein said complex is subjected to said field for a time sufficient to extend said sample oligonucleotide sequence and the position of said probe in relation to said anchor sequence is also determined.

9. The method of claim 1 additionally comprising subjecting the probe to a field which concentrates the probe near the anchor sequence during step (a).

10. The method of claim 1 wherein said probe is from about 4 to about 100 bases.

11. A method for determining whether a first and a second target oligonucleotide sequence are on a molecule of sample DNA comprising:
    (a) contacting said sample DNA with an anchor sequence comprising an oligonucleotide sequence which is immobilized to a support and which hybridizes with said first target oligonucleotide sequence and with a probe which hybridizes with said second target oligonucleotide sequence in a suitable buffer to form a complex;
    (b) subjecting said complex to an electric field which moves unbound oligonucleotide sequences away from said anchor sequence in the direction of said field; and
    (c) determining whether said probe is bound to said sample DNA.

12. The method of claim 11 wherein said sample DNA is not more than about 200 kilobases.

13. The method of claim 11 wherein said sample DNA greater than about 200 kilobases and said sample DNA is prepared by lysing cells in a gel and adding a fragment of said gel to said support.

14. The method of claim 11 wherein said probe is from about 5 to about 15 bases.

15. The method of claim 11 wherein said electric field extends said sample DNA in the direction of said field and the distance between said first and second oligonucleotide sequences is determined by determining the distance between said anchor sequence and said probe.

16. The method of claim 11 wherein hybridization of said sample DNA to said anchor sequence forms a double stranded oligonucleotide sequence having a site recognized by a restriction endonuclease and said restriction endonuclease is present on said solid phase or in said buffer.

17. A method for obtaining a pattern characteristic of sample DNA comprising:
    (a) contacting said sample DNA with an anchor sequence comprising an immobilized, conserved oligonucleotide sequence which hybridizes with said sample DNA and with a plurality of probes, each of said probes comprising an oligonucleotide sequence of from about 5 to about 15 bases in a suitable buffer to form a complex;

(b) subjecting said complex to an electric field which moves unbound oligonucleotide sequences away from said anchor sequence and extends said sample DNA in the direction of said field; and (c) determining the positions of said probes from said anchor sequence.

18. The method of claim 17 wherein said probes are from about 7 to about 10 bases.

19. The method of claim 17 wherein said probes have identical oligonucleotide sequences.

20. The method of claim 17 wherein the oligonucleotide sequence of said probe is a random sequence.

21. The method of claim 17 wherein said probes have different oligonucleotide sequences and are labeled with different fluorochromes.

22. A method for determining whether sample DNA and test DNA are from the same individual comprising:

(a) contacting said sample DNA and said test DNA with an anchor sequence comprising an immobilized, conserved oligonucleotide sequence which hybridizes with said test DNA and with a plurality of probes, each of said probes comprising an oligonucleotide sequence of from about 5 to about 15 bases in a suitable buffer to form a complex;

(b) subjecting said complex to an electric field which moves unbound oligonucleotide sequences away from said anchor sequence and extends said sample DNA in the direction of said field;

(c) determining the positions of said probes from said anchor sequence for said sample DNA and said test DNA; and (d) comparing the positions of said probes for said test DNA to said probes for said sample DNA.

23. A method for determining whether a putative father is the father of a child comprising:

(a) contacting said sample DNA from said putative father, said child and the mother of said child with an anchor sequence comprising an immobilized, conserved oligonucleotide sequence which hybridizes with said putative father's DNA and with a plurality of probes, each of said probes comprising an oligonucleotide sequence of from about 5 to about 15 bases in a suitable buffer to form a complex;

(b) subjecting said complex to an electric field which moves unbound oligonucleotide sequences away from said anchor sequence and extends said sample DNA in the direction of said field;

(c) determining the positions of said probes from said anchor sequence for said DNA from said putative father, said child, and said mother;

(d) comparing the positions of said probes for said child's DNA to those of said mother; and (e) comparing any positions of the probes of said child which do not match with the probes of said mother to said probes of said putative father.

24. A method for determining whether a test oligonucleotide sequence is present in sample oligonucleotide sequence comprising:

(a) contacting said sample oligonucleotide sequence with an anchor sequence comprising an immobilized, conserved oligonucleotide sequence known to hybridize with an oligonucleotide sequence present in said sample oligonucleotide sequence and with a probe comprising an oligonucleotide sequence which binds to said test oligonucleotide sequence in a suitable buffer to form a complex;

(b) subjecting said complex to an electric field which moves unbound oligonucleotide sequences away from said anchor sequence and extends said sample DNA in the direction of said field; and (c) determining whether said probe is bound to said sample oligonucleotide sequence.

25. The method of claim 24 wherein said sample oligonucleotide sequence is single stranded DNA.

26. The method of claim 24 wherein said sample oligonucleotide sequence is RNA.

27. The method of claim 24 wherein said probe is from about 20 to about 30 bases.

28. The method of claim 24 wherein said method additionally comprises the step of determining the distance of said probe from said anchor sequence.

29. The method of claim 24 wherein a plurality of probes which bind to a plurality of different test oligonucleotide sequences are used.

30. The method of claim 29 wherein said each of said probes is labeled with a different label.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 31 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:1:

TGAATTCAAA GGAAAACATA AGATGCAATT C  31

(2) INFORMATION FOR SEQ ID NO:2:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:2:

GAATTGCATC TTATGTTTTC CTTTGAATTC A  31

(2) INFORMATION FOR SEQ ID NO:3:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:3:

GAAGGAATGT TC  12

(2) INFORMATION FOR SEQ ID NO:4:

(i) SEQUENCE CHARACTERISTICS:
(A) LENGTH: 7 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

TTGAATT  7

(2) INFORMATION FOR SEQ ID NO:5:

(i) SEQUENCE CHARACTERISTICS:
(A) LENGTH: 7 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

GTTGCAA  7

(2) INFORMATION FOR SEQ ID NO:6:

(i) SEQUENCE CHARACTERISTICS:
(A) LENGTH: 7 base pairs
(B) TYPE: nucleic acid
(C) STRANDEDNESS: single
(D) TOPOLOGY: linear (ii) MOLECULE TYPE: DNA (genomic)

( x i ) SEQUENCE DESCRIPTION: SEQ ID NO:6:

CGGCTCG                                                                                                           7

( 2 ) INFORMATION FOR SEQ ID NO:7:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CGGACTG                                                                                                           7

( 2 ) INFORMATION FOR SEQ ID NO:8:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GATAGGA                                                                                                           7

( 2 ) INFORMATION FOR SEQ ID NO:9:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

ATGGGAG                                                                                                           7

( 2 ) INFORMATION FOR SEQ ID NO:10:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

AGGAACG                                                                                                           7

( 2 ) INFORMATION FOR SEQ ID NO:11:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CGCGCCCTCG TATCAC                                                                                                 16

( 2 ) INFORMATION FOR SEQ ID NO:12:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:12:

CGCGAGGTCG CCGCCC    16

( 2 ) INFORMATION FOR SEQ ID NO:13:

( i ) SEQUENCE CHARACTERISTICS:
      ( A ) LENGTH: 12 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:13:

AACACCGATG AT    12